United States Patent [19]
Spivey et al.

[11] Patent Number: 5,886,353
[45] Date of Patent: *Mar. 23, 1999

[54] IMAGING DEVICE

[75] Inventors: Brett Spivey, Encinitas; Peter Martin, La Jolla; A. Lee Morsell, Del Mar; Eugene Atlas, Carlsbad, all of Calif.; Anthony Pellegrino, New Fairfield, Conn.

[73] Assignee: ThermoTrex Corporation, San Diego, Calif.

[*] Notice: This patent issued on a continued prosecution application filed under 37 CFR 1.53(d), and is subject to the twenty year patent term provisions of 35 U.S.C. 154(a)(2).

The term of this patent shall not extend beyond the expiration date of Pat. No. 5,528,043.

[21] Appl. No.: 668,432

[22] Filed: Jun. 18, 1996

Related U.S. Application Data

[63] Continuation-in-part of Ser. No. 426,691, Apr. 21, 1995, Pat. No. 5,528,043 and a continuation-in-part of PCT/US96/05617 Apr. 22, 1996.

[51] Int. Cl.[6] ............................... G01T 1/24; H01L 27/14
[52] U.S. Cl. ................. 250/370.09; 250/580; 250/208.1; 378/98.8
[58] Field of Search ......................... 250/370.08, 370.09, 250/580, 208.1, 370.14; 378/98.8

[56] References Cited

U.S. PATENT DOCUMENTS

| H1105 | 9/1992 | Jebo et al. . | |
|---|---|---|---|
| 4,841,348 | 6/1989 | Shizukuishi et al. | 257/226 |
| 4,958,363 | 9/1990 | Nelson et al. . | |
| 4,969,175 | 11/1990 | Nelson et al. . | |
| 4,997,750 | 3/1991 | Dickerson et al. . | |

(List continued on next page.)

OTHER PUBLICATIONS

Baji, et al., "Solid–State Color Image Sensor Using Hydrogenated Amorphous Silicon", Proc. 13th Conf. Solid State Devices, Tokyo, 1981 , Jpn. J. Appl. Phys. 21 (1982) 21–1, pp. 269–273.

Fischer, J., et al., "Thin Film on ASIC—A Novel Concept for Intelligent Image Sensors", *Mat. Res. Soc. Symp. Pros.*, vol. 258 (1992), pp. 1139–1141.

Stiebig, H., et al., "Simulation of a–Si:H Color Sensors for Application in Intelligent Sensor Systems", *Mat. Res. Soc. Symp. Proc.*, vol. 297 (1993) pp. 963–968.

Fischer, Helmut, et al., "Analog Image Detector in Thin Film on ASIC (TFA)–Technology", *SPIE*, vol. 2247 (1994), pp. 282–291.

Schulte, Jurgen, et al., "Intelligent Image Sensor for On–Chip Contour Extraction", *SPIE*, vol. 2247, (1994), pp. 292–300.

Zhu, Qi, et al., "New Type of Thin Film Color Image Sensor", *SPIE*, vol. 2247 (1994), pp. 301–310.

(List continued on next page.)

*Primary Examiner*—Constantine Hannaher
*Attorney, Agent, or Firm*—Fish & Richardson P.C.

[57] ABSTRACT

An imaging device for producing images from electron-hole producing radiation. Electron-hole pairs are produced in a radiation absorbing layer comprised of a photoconductive material. This layer covers an array of metal oxide semiconductor pixel circuits which are incorporated into and on a crystalline semiconductor substrate. Each pixel circuit has a charge collecting pixel electrode, a capacitor connected to the electrode to store the charges and a charge measuring transistor circuit. A voltage source provides an electric field across the radiation absorbing layer between the pixel electrodes and a radiation transparent surface electrode covering the radiation absorbing layer. A data acquisition system acquires and stores data derived from charge measurements and in a preferred embodiment a computer computes images from the data. The image may be displayed on a monitor or printed out on a printer. Preferred embodiments provide images from x-ray, ultraviolet and visible light.

84 Claims, 25 Drawing Sheets

U.S. PATENT DOCUMENTS

| | | |
|---|---|---|
| 5,021,327 | 6/1991 | Bunch et al. . |
| 5,040,546 | 8/1991 | Deluhery . |
| 5,150,394 | 9/1992 | Karellas . |
| 5,228,068 | 7/1993 | Mazess . |
| 5,235,195 | 8/1993 | Tran et al. . |
| 5,254,480 | 10/1993 | Tran ............................. 250/370.09 X |
| 5,287,546 | 2/1994 | Tesic et al. . |
| 5,291,537 | 3/1994 | Mazess . |
| 5,295,176 | 3/1994 | Deslattes . |
| 5,305,368 | 4/1994 | Bisek et al. . |
| 5,306,306 | 4/1994 | Bisek et al. . |
| 5,352,897 | 10/1994 | Horikawa et al. ............ 250/370.09 X |
| 5,381,458 | 1/1995 | Deslattes . |
| 5,399,470 | 3/1995 | Dickerson et al. . |
| 5,400,387 | 3/1995 | Gard et al. . |
| 5,418,832 | 5/1995 | Barnes . |
| 5,465,284 | 11/1995 | Karellas . |
| 5,480,439 | 1/1996 | Bisek et al. . |
| 5,481,587 | 1/1996 | Mazess . |
| 5,509,042 | 4/1996 | Mazess . |
| 5,519,227 | 5/1996 | Karellas . |
| 5,528,043 | 6/1996 | Spivey et al. ...................... 250/370.09 |
| 5,530,735 | 6/1996 | Gard et al. . |
| 5,533,084 | 7/1996 | Mazess . |
| 5,572,034 | 11/1996 | Karellas . |
| 5,572,037 | 11/1996 | Liu et al. . |
| 5,577,089 | 11/1996 | Mazess . |

OTHER PUBLICATIONS

Zhu, Q., et al., "A Novel a–Si(C):H Color Sensor Array", *Mat. Res. Soc. Symp. Proc.*, vol. 336 (1994), pp. 843–847.

Fischer, H., et al., "Technology and Performance of TFA (Thin Film on ASIC)–Sensors", *Mat. Res. Soc. Symp. Proc.*, vol. 336 (1994), pp. 867–872.

Aw, Chye Huat, et al., "A 128 +128–Pixel Standard–CMOS Image Sensor with Electronic Shutter", *IEEE Journal of Solid–State Circuits*, vol. 31, No. 12 (Dec. 1996), pp. 1922–1930.

Nixon, R.H., "256 +256 CMOS Active Pixel Sensor Camera–on–a–Chip", *IEEE Journal of Solid–State Circuits*, vol. 31, No. 12 (Dec. 1996), pp. 2046–2050.

Mendis, Sunetra K., et al., "CMOS Active Pixel Image Sensors for Highly Integrated Imaging Systems", *IEEE Journal of Solid–State Circuits*, vol. 32, No. 2 (Feb. 1997), pp. 187–197.

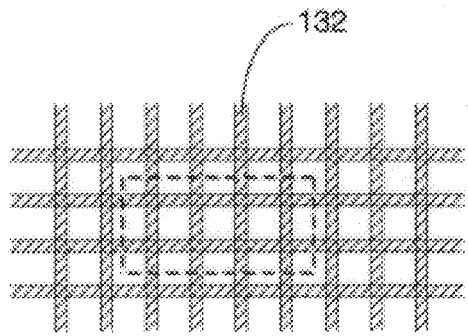
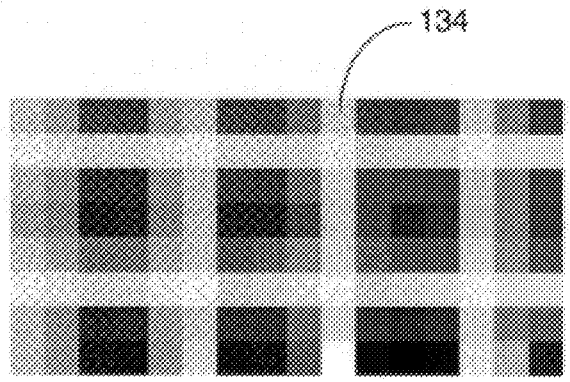
FIG. 13A　　　　　　　　FIG. 13B
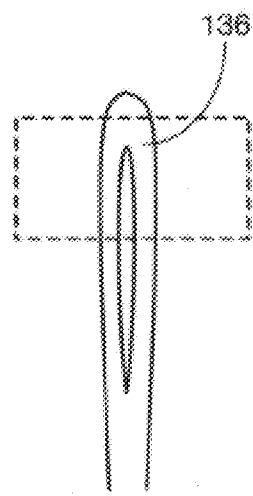
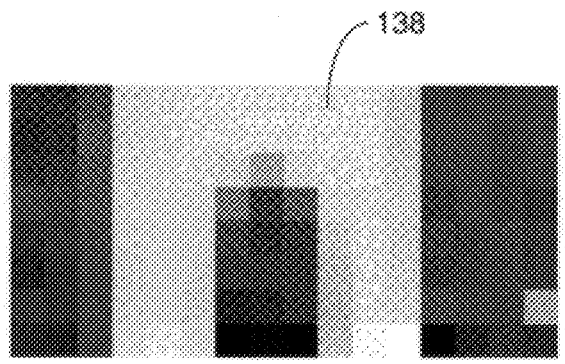
FIG. 14A　　　　　　　　FIG. 14B

IMAGING DEVICE

The present invention relates to imaging devices and specifically to devices for forming images from radiation. This application is a continuation-in-part U.S. application of Ser. No. 08/426,691, filed Apr. 21, 1995 now U.S. Pat. No. 5,528,043 and International Application No. PCT/US96/05617 with an international filing date of Apr. 22, 1996.

BACKGROUND OF THE INVENTION

Film-screen x-ray imaging devices employing photographic film are widely used for medical imaging. However, the film is often overexposed in some areas and underexposed in other areas due to the limited range of contrast of the film combined with the thickness and composition variations of the tissue across the image. Discrimination of contrast differences of soft tissue in the overexposed and underexposed areas of the film can be difficult. This problem is especially apparent in film-screen mammography.

Attempts have been made at replacing film with electronic image sensors. Potential advantages of electronic image sensors over film include more accurate measurement of x-ray intensity over greater ranges, ability to digitize the image data, ease of archiving and transmitting image data, and improved display capabilities.

However, widespread clinical deployment of digital x-ray radiology has been hampered by the lack of a relatively inexpensive, compact, digital x-ray image sensor of sufficient image size and resolution. Present digital x-ray imaging systems typically use a fluorescing plate that converts each x-ray photon into a large number of visible light photons to produce a visible light image. The visible light image is then imaged onto an optical image sensor such as a CCD. The imaging performance of these techniques is degraded by relatively low x-ray to visible light conversion efficiencies, low collection efficiencies of the light photons, additional quantum noise from the light photons, and loss of resolution due to light spreading in the x-ray to visible light converter.

It is known that selenium is a photoconductive substance, i.e. x-ray photons absorbed in a layer of selenium exposed to an electric field will create a number of electron/hole pairs permitting a current to flow through the otherwise insulating layer. Xerox Corporation developed an x-ray imaging device in which an x-ray induced charge distribution on a selenium-coated aluminum plate is recorded with a paper/toner process. Philips Corporation presently markets a chest x-ray imager in which an x-ray induced charge distribution on a selenium-coated aluminum plate is recorded with scanning electrometers.

Metal oxide semiconductor (MOS) fabrication technology is a well established industry which involves fabrication of integrated circuits on and in the upper surface of a wafer of crystalline silicon. Complimentary metal oxide semiconductor (CMOS) technology combines both n-channel and p-channel transmitters on a single wafer. MOS technology typically utilizes a single crystal silicon substrate as the semiconductor material for transistor fabrication. When we use the term "single crystal silicon substrate" in this application we are referring to a substrate comprised of silicon atoms arranged in a regular crystalline lattice with relatively few defects. The high mobility of charge carriers and well-defined energy bandgap in single crystal silicon results in fast, compact, low-noise circuitry. Other crystalline semiconductor materials are available for use as substrates for metal oxide semiconductor fabrication. These include crystalline silicon on an electrical insulator (such as silicon oxide or sapphire) aluminum gallium, arsenide, and indium gallium arsenide.

Thin film transistor (TFT) technology is an emerging semiconductor fabrication technology in which transistors are fabricated using a thin film of semiconductor material such as amorphous silicon, polycrystalline silicon or amorphous cadmium selenide deposited on an insulating substrate. An advantage of TFT technology is the potential for large area circuits. However, the disordered molecular structure of these thin films leads to low charge mobility and a certain density of localized energy states within the energy bandgap. In comparison with CMOS circuits, TFT circuits are generally slow and noisy with large leakage currents.

Various approaches are presently being proposed and investigated for directly acquiring a digital x-ray image. For example, Zhao and Rowlands (Proc. SPIE 1993; 1896: 114–120) have proposed a readout array fabricated using cadmium selenide TFT technology with an amorphous selenium coating. Tran et. al. disclose, in U.S. Pat. No. 5,235,195, TFT array circuits coated first with a "planarization" layer which in turn is coated with an energy-sensitive layer. A need still exists for improved x-ray imaging devices the present invention provides such a device.

SUMMARY OF THE INVENTION

The present invention provides an imaging device for producing images from electron-hole producing radiation. Electron-hole pairs are produced in a radiation absorbing layer of a photoconductive material. This layer covers an array of metal oxide semiconductor pixel circuits which are incorporated into and on a semiconductor substrate. Each pixel circuit has a charge collecting pixel electrode, a capacitor connected to the electrode to store the charges and a charge measuring transistor circuit. A voltage source provides an electric field across the radiation absorbing layer between the pixel electrode and a radiation transparent surface electrode covering the radiation absorbing layer. A data acquisition system acquires and stores data derived from charge measurements and a computer computes images from the data.

The image may be displayed on a monitor or printed out on a printer. Preferred embodiments provide images from x-ray, ultra-violet and visible light. Images can also be provided utilizing particle radiation. Advantages of this invention over the prior art TFF technology results from our exploitation of the many benefits of metal oxide semiconductor technology. These advantages include much better circuit performance as well as design flexibility which enables us, in a preferred embodiment, to fabricate a pixel array and readout circuitry together on a single wafer of silicon.

BRIEF DESCRIPTION OF THE DRAWINGS

FIGS. 13A and 13B are drawings of a wire screen and an x-ray image of the wire screen acquired with the first preferred embodiment.

FIGS. 14A and 14B are drawings of a portion of sewing needle and an x-ray image of a portion of the needle acquired with the first preferred embodiment.

DETAILED DESCRIPTION OF PREFERRED EMBODIMENTS

Basic Concept

Figure 1:
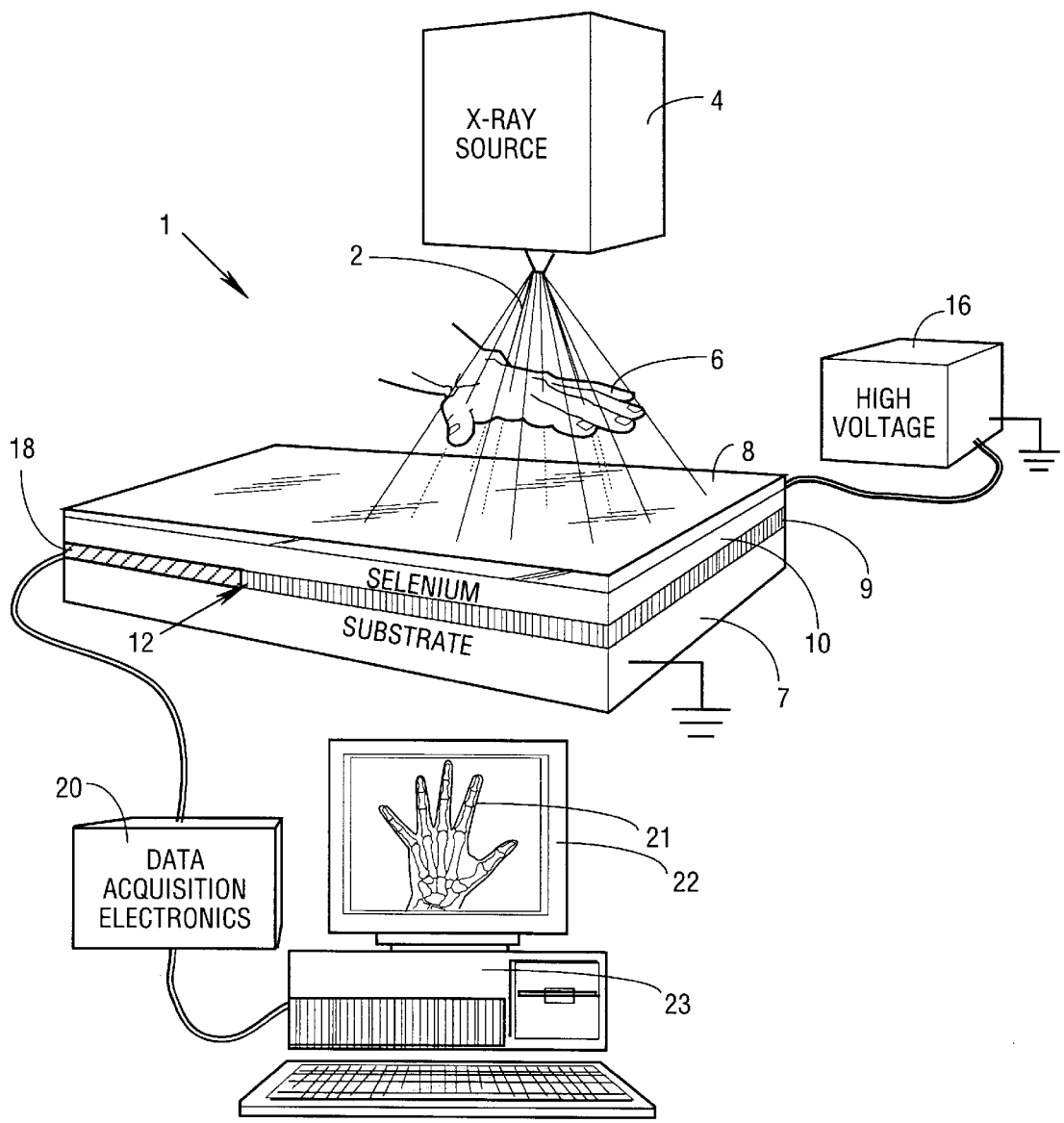
FIG. 1 is a diagram showing the principal elements of a preferred embodiment of the present invention.

Preferred embodiments of this invention can be described by reference to FIG. 1 and FIGS. 2A through 2D. X-ray photons 2 produced by x-ray source 4 directed toward target 6 are either absorbed in or pass through target 6. Most of the x-ray photons which pass through target 6 also pass through x-ray transparent conductive layer 8 and are absorbed in absorbing layer 10 of x-ray sensor 1. Each absorbed x-ray photon in the process of being absorbed creates a large number of electron/hole pairs in absorbing layer 10 in the immediate vicinity of the absorption. An electric potential applied between the transparent conductive layer 8 and individual electrodes 14 in pixel array 9 by voltage source 16 forces holes from these electron/hole pairs to migrate to individual electrodes 14 located in pixel array 9. Pixel array 9 and readout circuit 18 together form electronic readout array 12 and are fabricated on and in the upper surface of a single substrate 7 of crystalline silicon. Electronic signals from the electronic readout array 12 representative of the x-ray photons absorbed in the absorbing layer 10 are directed from pixel array 9 through readout circuit 18 to data acquisition electronics 20 where the electronic signals are converted into digital data which is stored in computer 23. An image is computed from the data utilizing software in computer 23, and the x-ray image 21 of target 6 is displayed on monitor 22.

Figure 2A:
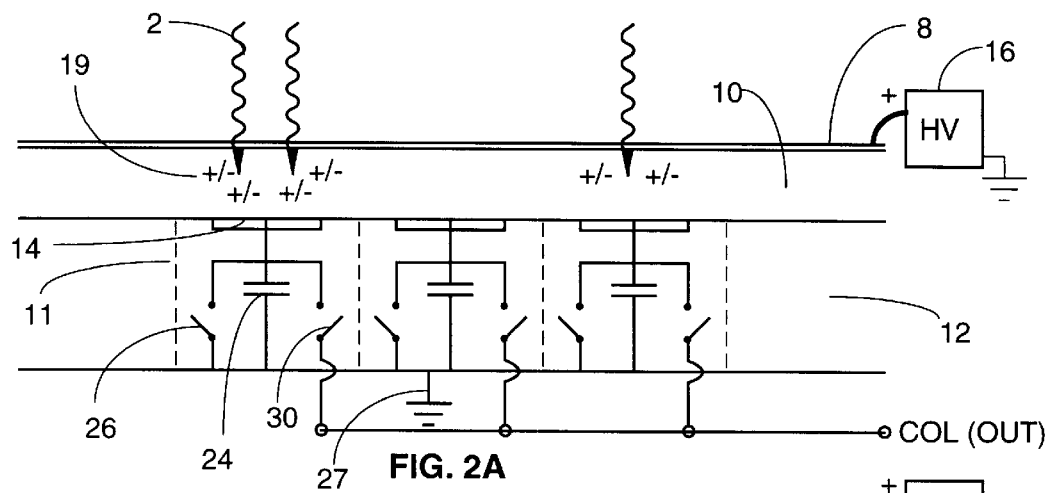
FIGS. 2A through 2D are circuit diagrams showing the basic operating conditions of the invention.
Figure 2B:
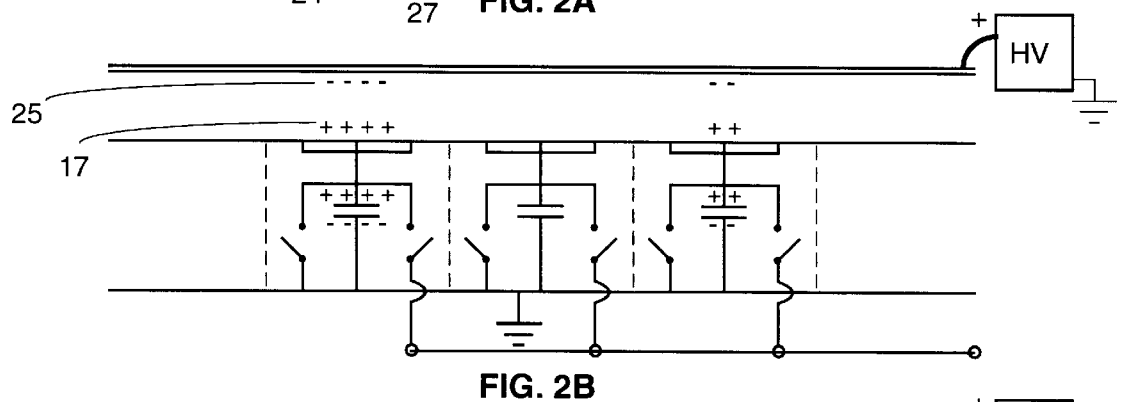
Figure 2C:
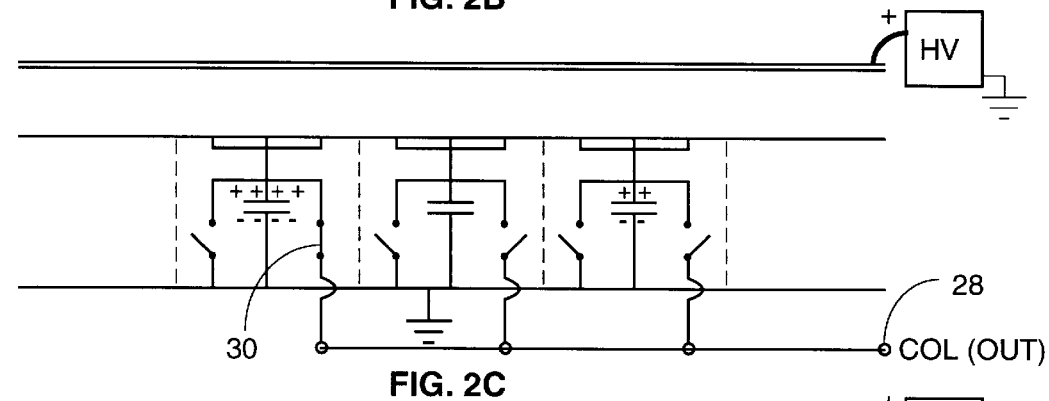
Figure 2D:
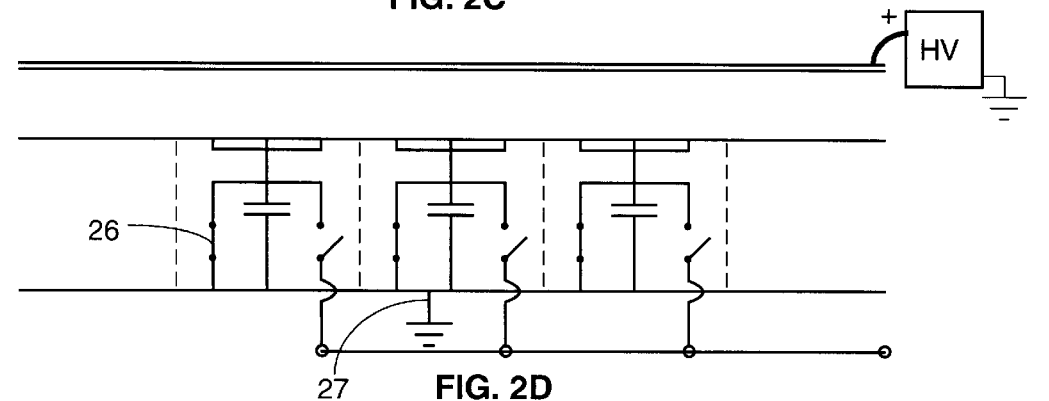

Each pixel in pixel array 9 is comprised of an individual electronic pixel circuit 11. Three of these pixel circuits 11 (segregated by dashed lines) are depicted in FIGS. 2A through 2D. FIG. 2A shows three x-ray photons 2 passing through transparent conductive layer 8 and being absorbed in the absorbing layer 10, each x-ray photon liberating electron/hole pairs in the immediate vicinity of the absorbed x-ray photon. For example, in an amorphous selenium layer a typical x-ray photon of intermediate x-ray energy will liberate about one hundred electron/hole pairs. In FIGS. 2A–D we represent these one hundred electron/hole pairs with two + and two– signs. As shown in FIG. 2B a positive electric potential applied to layer 8 forces the positive charges (holes) 17 to migrate downward to electrode 14 in pixel circuit 11 and the negative charges (electrons) 25 to migrate upward to the conduction layer 8. The voltage applied by source 16 is large enough so that there is very little lateral spreading of holes 17. Electrodes 14 collect the positive charges 17 and store the charges on capacitors 24, thus creating voltages across capacitors 24 which are proportional to the collected charges 17. As suggested by FIG. 2C, the collected positive charge 17 (and therefore the voltage across the capacitor 24) remains substantially constant after the x-ray source 4 is turned off. The voltage across each pixel capacitor 24 is non-destructively recorded by sequentially closing select switch 30 at each pixel circuit 11 in order to place the voltage on capacitor 24 onto output line 28 as Col(out). FIG. 2D shows that the collected charge 17 at all pixel circuits 11 can then be simultaneously drained to ground 27 by closing all of the reset switches 26 and shorting all of the capacitors 24 to ground 27.

The reader should note that in the above description conductive layer 8 is charged positive by high voltage supply 16. We could reverse the polarity of the sensor by charging conductive layer 8 negative. In this case electrons would be collected on electrodes 14 and the resulting negative charges could be utilized by similar electronic circuitry to produce images.

PROTOTYPE 8×16 PIXEL SENSOR

Figure 4:
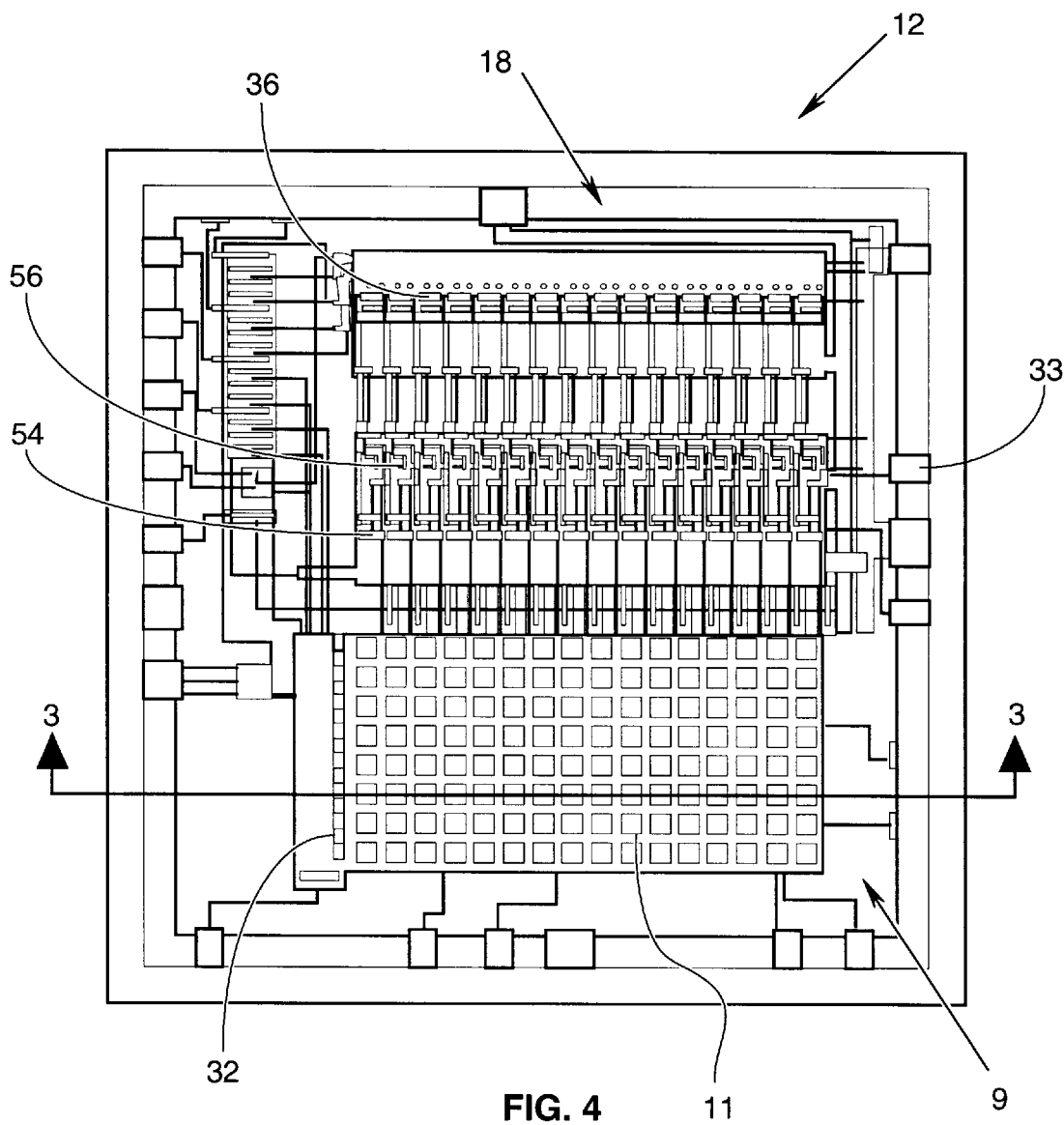
FIG. 4 shows a top view of the prototype electronic readout array.
Figure 3:
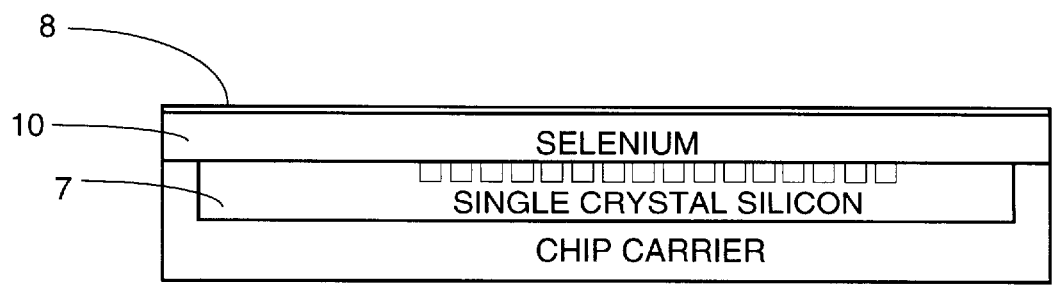
FIG. 3 is a cross sectional drawing of a prototype sensor fabricated and tested by the inventors.

FIGS. 3 and 4 are drawings of a first preferred embodiment of the present invention. This embodiment is a small 8×16 pixel prototype digital x-ray image sensor which has been fabricated and tested by the inventors and their fellow workers. The elements include pixel array 9 with 128 pixel circuits 11 arranged in an 8×16 array. The size of each pixel circuit 11 is 66 microns×66 microns (roughly the diameter of a human hair) resulting in a total imaging area of 0.5 mm×1 mm. Readout circuit 18 includes shift register 32 to select a row of pixel circuits 11 of the pixel array 9 for readout purposes. The readout circuit 18 also includes a shift register 36 for column selection, sample-and-hold circuits 54, bilateral switches 56, and pixel reset circuitry. Pixel array 9 and readout circuit 18, which together constitute electronic readout array 12, are fabricated in and on a substrate 7 of single crystal silicon. Wire bond pads 33 at the periphery of the electronic readout array 12 connect the readout circuit 18 to data acquisition electronics 20 as shown in FIG. 1. Pixel array 9 and readout circuit 18 are coated with a uniform layer of amorphous selenium 10 which is in turn coated with a conductive electrode layer 8. Electrode layer 8 is in this embodiment a very thin layer of silver which is substantially transparent to x-rays.

Sensor Circuitry

Figure 5:
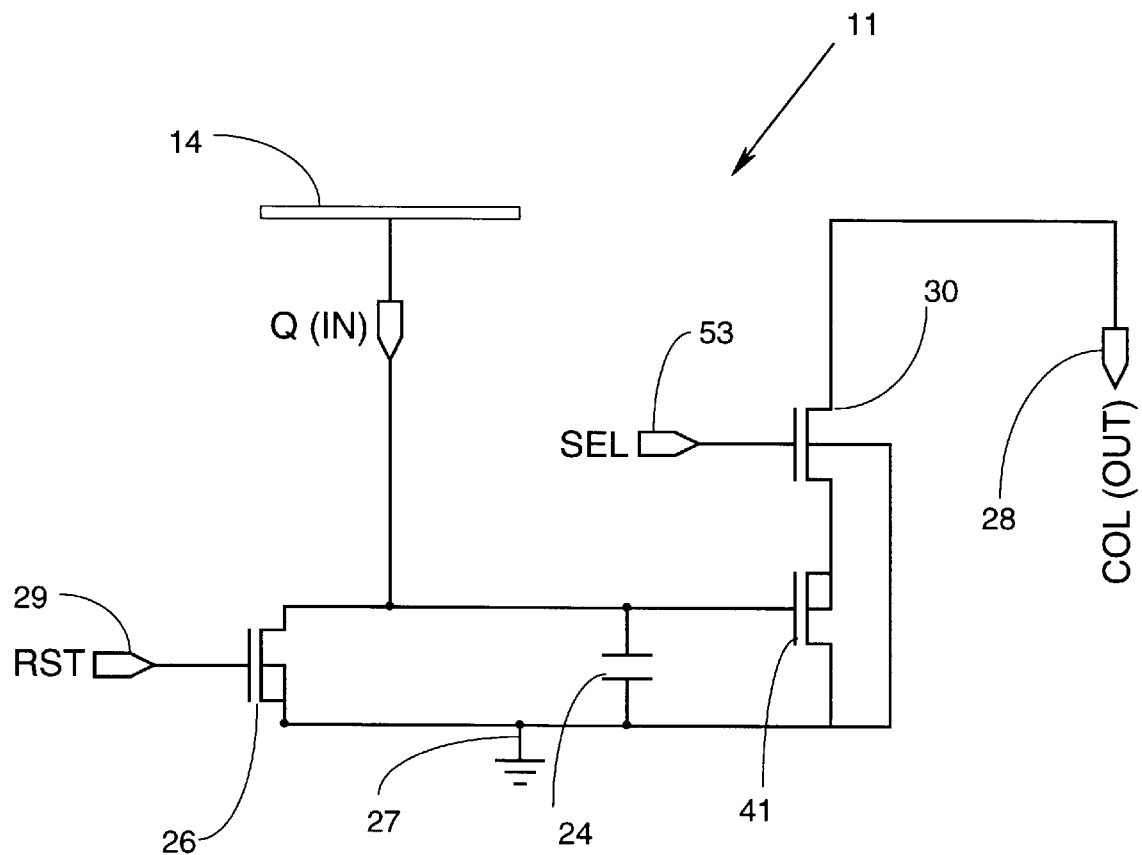
FIG. 5 is a circuit diagram of the elements in an individual pixel of the pixel array of the prototype readout array.

The circuit diagram of an individual pixel circuit 11 is displayed in FIG. 5. The charge Q(in) collected via electrode 14 charges 345 femtofarad capacitor 24 resulting in a voltage proportional to the collected charge Q(in). Source-follower transistor 41 acts as a buffer for this voltage and allows for a non-destructive readout. A digital selection signal SEL applied at line 53 causes selection transistor 30 to turn on and connect the source of source-follower transistor 41 with column readout line 28. Then, source-follower transistor 41 acts together with current source transistor 110 at the edge of the array (see FIG. 8) to establish a voltage COL(out) on the column readout line 28 which follows the voltage on capacitor 24 with a small (approximately 0.5 Volt) positive voltage offset. After the charge on capacitor 24 has been read out, reset signal RST applied at line 29 enables reset transistor 26 to turn on and to drain the charge from capacitor 24 to ground 27.

Figure 6:
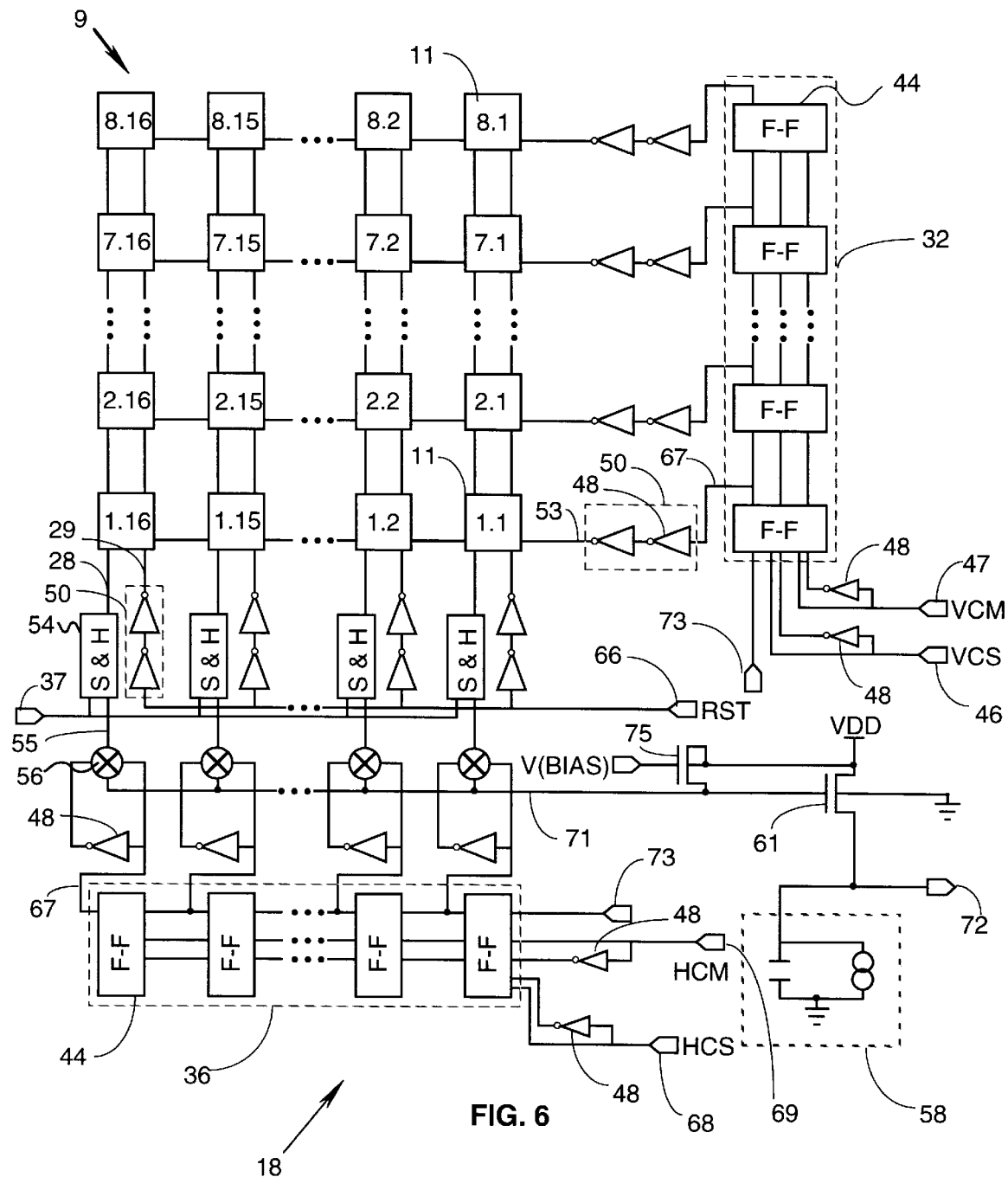
FIG. 6 is a schematic diagram of the electronic readout array utilized in the prototype embodiment.

The circuit diagram for the entire electronic readout array 12 can be described by reference to FIGS. 5 through 8. A schematic diagram for the electronic readout array 12, including the pixel array 9 and the readout circuit 18, is shown in FIG. 6. The primary circuit components include 128 identical pixel circuits 11 forming pixel array 9, row-select shift register 32, column-select shift register 36, sixteen sample-and-hold circuits 54, and sixteen bilateral switches 56.

The voltage on capacitor 24 of each pixel circuit 11 is sequentially recorded by the readout circuit 18 in the following manner. The entire first row (1.1, 1.2, . . . , 1.16) of pixel circuits 11 is selected when row-select shift register 32 activates row-select line 53 through buffer 50 which closes selection transistor 30 of each pixel 11 in the first row. Buffer 50 is comprised of two conventional inverter circuits 48. Each pixel circuit 11 in the first row is then sequentially and non-destructively read out in two steps. First, the voltages on column readout line 28 of the sixteen pixel circuits 11 (1.1, 1.2, . . . , 1.16) are simultaneously sampled each by a separate sample-and-hold circuit 54, when a digital signal is simultaneously applied to sample-and-hold circuits 54 at line 37. This sampling process produces a voltage at the output line 55 of each sample-and-hold circuit 54 (described below) which is identical to the voltage at each column readout line 28 except for a small (approximately 1 Volt) positive voltage offset. Second, the voltages at output lines 55 sampled by the sixteen sample-and-hold circuits 54 are sequentially connected to the output line 71 by bilateral switches 56, controlled by column-select shift register 36 (described below). The voltages present at output line 71, for which transistor 75 acts as a pull-up resistor, are buffered with source-follower transistor 61, which is supplied with drain current source 58. The resulting analog voltage signals at output line 72 are sent to data acquisition electronics 20. The readout process continues by sequential selection of the remaining 7 rows of pixel circuits 11, and voltage data from these rows is collected in a similar manner. There is no shifting of charge from the pixel circuits 11 to the readout circuit 18, as in the case of a CCD array. This feature of our CMOS array allows for a nondestructive readout and very low consumption of power.

The 8-cell row-select shift register 32 and 16-cell column-select shift register 36 have identical design features. The basic design comprises a string of master-slave flip-flop circuits 44, the output of one flip-flop 44 connected to input of the next flip-flop 44. The shift registers 32 and 36 sequentially shift a digital data signal (either high or low) from one flip-flop 44 to the next flip-flop 44 during each full cycle of a clock signals. Four synchronous, single-frequency clock lines connect in parallel to each flip-flop 44, one line each for the master clock CM, an inverted master clock CMB, a slave clock CS which is delayed one-half cycle from the master clock CM, and an inverted slave clock CSB. The input data line 73 is raised high during just one cycle of the clocks and then held low during subsequent clock pulses, and a single high signal moves along the shift register outputs 67 from one end of the shift register to the other. The row select shift register 32 is controlled by master clock VCM 47 and slave clock VCS 46 to sequentially select each row of the pixel array 9. The column-select shift register 36 is controlled by master clock HCM 69 and slave clock HCS 68 to sequentially select each bilateral switch 56.

Figure 7:
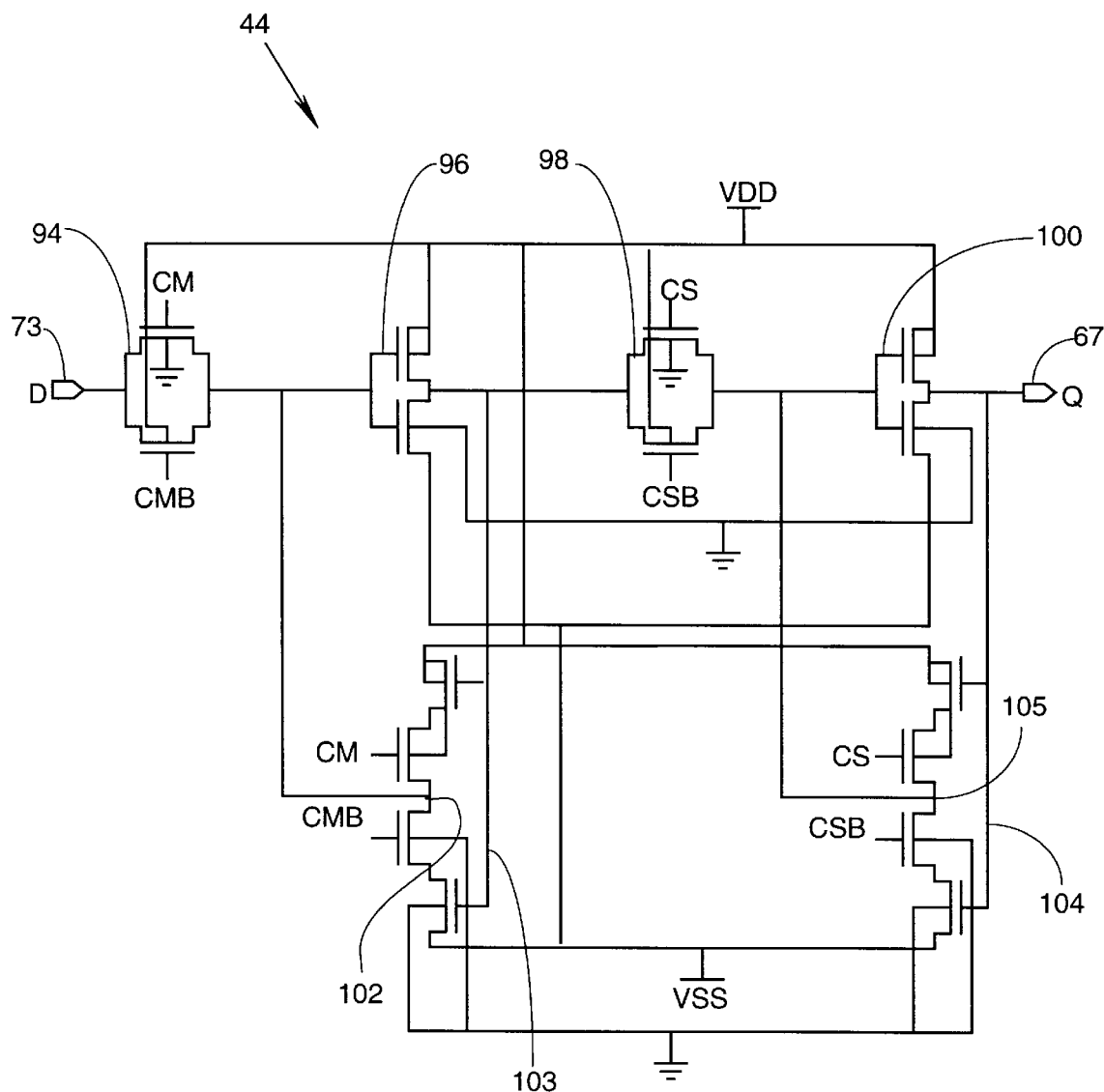
FIG. 7 is a circuit diagram of one cell of the shift register used in the readout circuitry.

FIG. 7 shows a circuit diagram of an individual master-slave flip-flop 44. The design includes two identical flip-flop circuits in series, one flip-flop controlled by the master clock CM and CMB and the next flip-flop controlled by the slave clock CS and CSB. The master flip-flop consists of bilateral switch 94, controlled by master clock CM and CMB, connected in series with inverter 96. Tri-state inverter 102 provides feedback to allow bistable operation of the master flip-flop. The slave flip-flop consists of bilateral switch 98, controlled by slave clock CS and CSB, connected in series with inverter 100. Tri-state inverter 104 provides feedback to allow bistable operation of the slave flip-flop. A logic signal (high or low) at the D input 73 of bilateral switch 94 is sent to the input of bilateral switch 98 by a single transition of master clock CM. A single transition of slave clock CS, which is slightly delayed with respect to the master clock, then sends the logic signal at the input to bilateral switch 98 to the output Q 67.

FIG. 8 is a schematic diagram of one of the sixteen sample-and-hold circuits 54 shown in FIG. 6. When a row of pixel circuits 11 is selected by shift register 32, selection transistors 30 in all the pixels in the row are turned on to connect the input 28 of each sample-and-hold circuit 54 with the source of source-follower transistor 41 on each pixel. Transistor 110, biased by external bias voltage V (bias), acts as a pull-up resistor for source-follower transistor 41 in pixel circuit 11 (see FIG. 5). Another source-follower transistor 112 in sample-and-hold circuit 54 buffers the voltage on input 28 and presents this voltage to the input of a bilateral analog switch 116. This switch 116, which allows current to flow in either direction when turned on by digital control signal SH 37, places the buffered voltage onto the 7.5 pF capacitor 117. Source-follower transistor 118 conveys the voltage on capacitor 117 to output line 55. Source-follower transistors 112 and 118 each have transistors 93, biased by external bias voltage V (bias), to act as pull-up resistors.

Sensor Fabrication

Electronic readout array 12 of the prototype sensor was fabricated using complimentary metal oxide semiconductor (CMOS) fabrication technology. CMOS fabrication technology is a well known integrated circuit fabrication technology and is described in many text books. A good description is also provided to in U.S. Pat. No. 3,356,858; to F. M. Wanlass (Issued Dec. 5, 1967). For our prototype device, the CMOS fabrication process begins with a wafer comprised of a single crystal of silicon, approximately 500 microns thick, which is doped with an electron-acceptor impurity, such as boron, in order to produce a p-type substrate 7. Field effect transistors (FET's) are produced on and in the upper one micron layer of the p-type silicon substrate 7. These transistors provide the basic circuit elements of the electronic readout array 12, shown in FIGS. 5 through 8, including digital and analog switches, current source transistors, and source-follower transistors. Passive electrical circuit components such as capacitors, resistors, transistor gates, and electrically conductive lines to connect the circuit components, are fabricated by adding alternating patterned layers of electrical insulators and conductors.

A typical CMOS process begins with the addition of patterned layers of electron-acceptor or electron-donor impurities, in substrate 7 to produce patterns of p-type or n-type regions, respectively. A p-type region has a surplus of mobile holes and an n-type region has a surplus of mobile electrons in the silicon crystal. Then, different patterned layers of insulating oxide, conductive polysilicon, and conductive metal are sequentially placed on substrate 7. The fabrication of each of these patterned layers requires many steps, including a coating the substrate with a specific layer, coating the layer with a light-sensitive organic film called photoresist, projecting a mask pattern onto the photoresist to sensitize it, selectively dissolving the photoresist to have a pattern matching the projected pattern, etching the layer below the photoresist in the open regions of the photoresist pattern, and finally, removing the remaining photoresist. The patterned n-type and p-type regions are produced by ion implantation through a patterned oxide layer.

Figure 9:
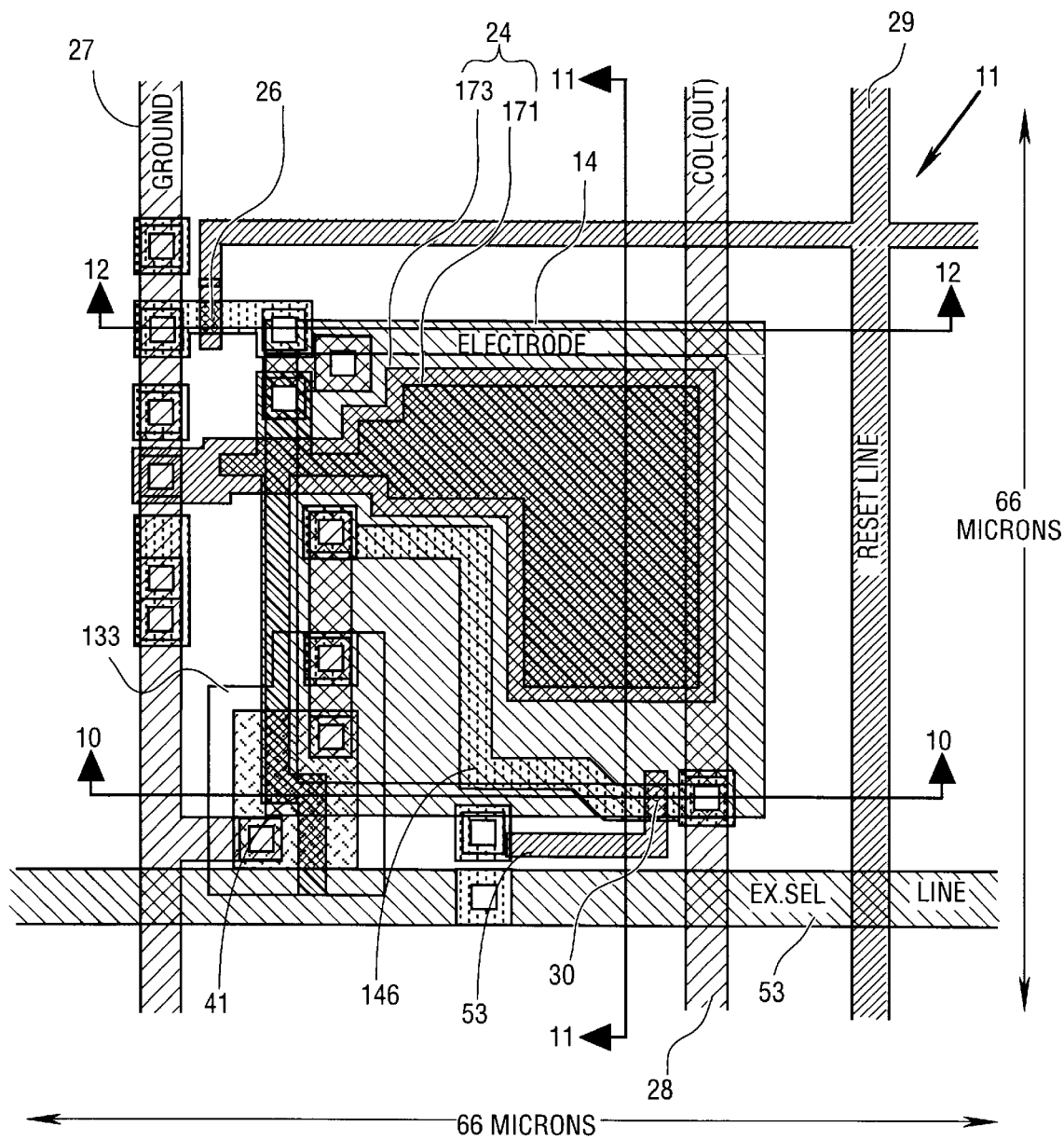
FIG. 9 shows a top view of the actual layout of the elements in an individual pixel of the pixel array.
Figure 10:
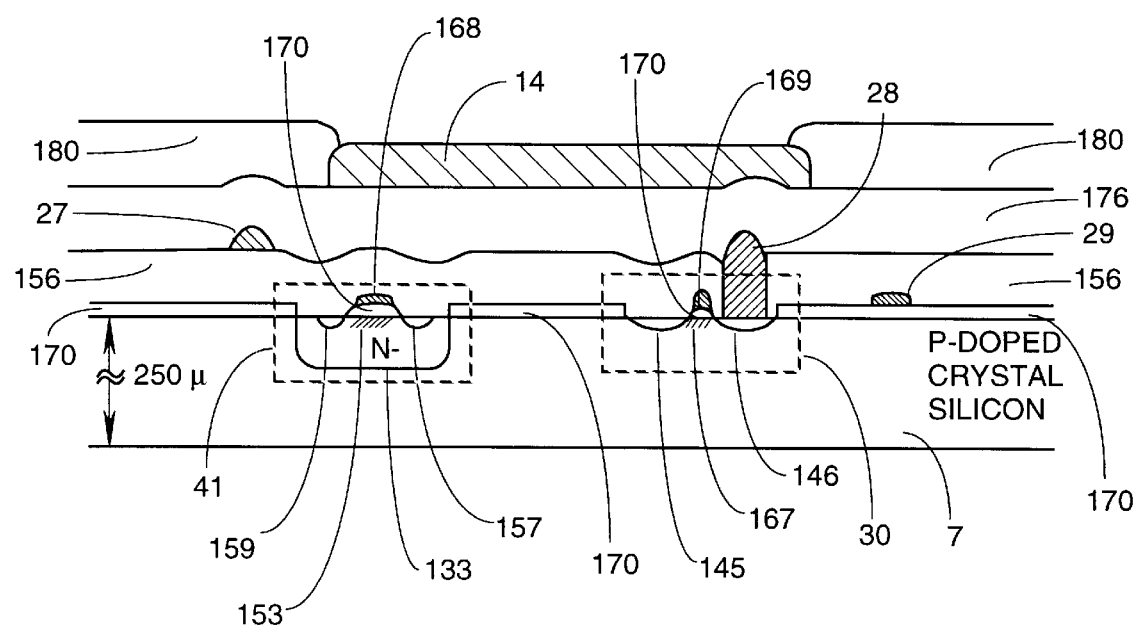
FIGS. 10–12 show three cross sections of the actual layout in an individual pixel of the pixel array.
Figure 11:
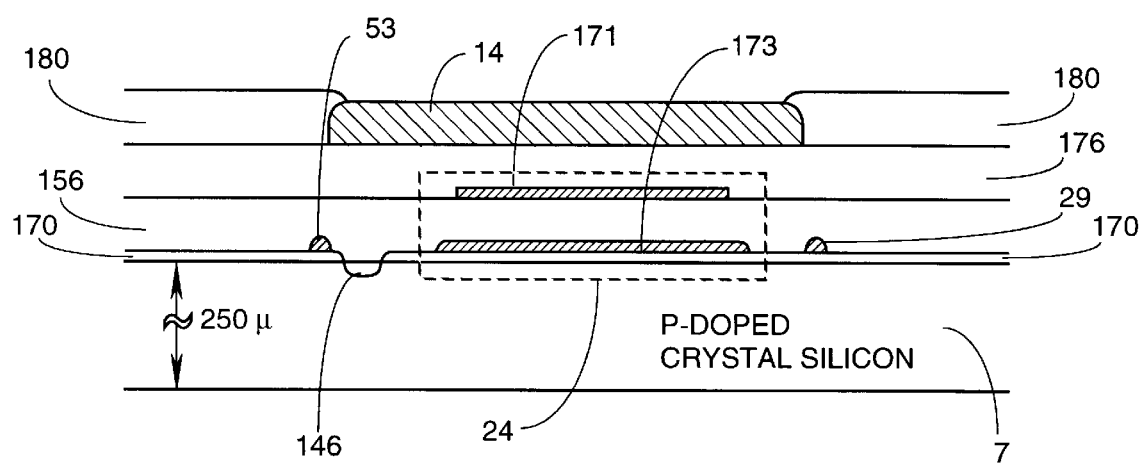
Figure 12:
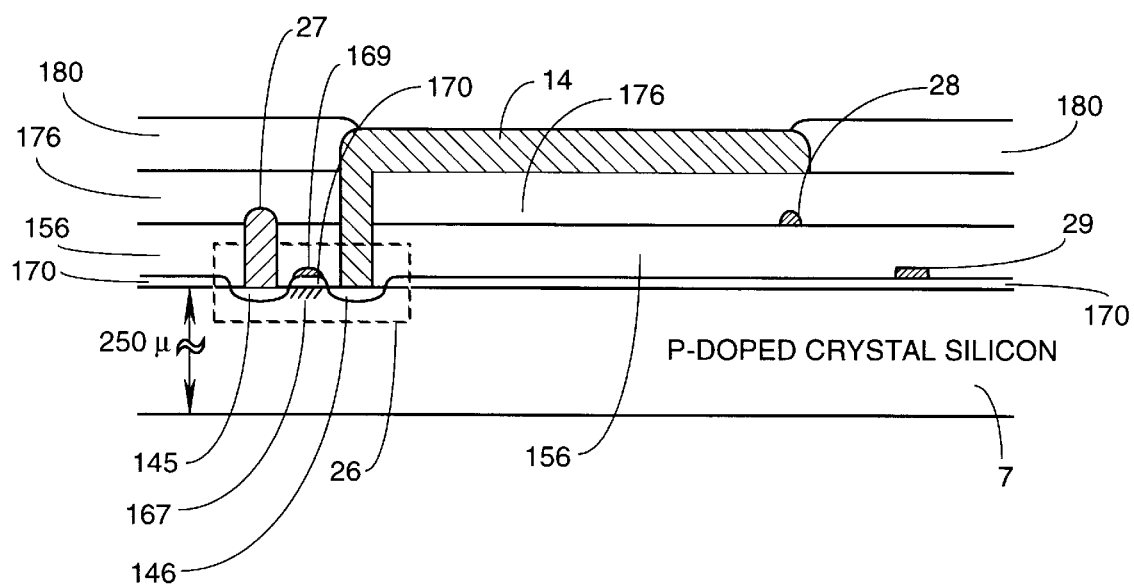

A top view of the layout of the electronic readout array 12 is shown in FIG. 4. This figure shows the layout of the 128 pixel circuits 11 of the pixel array 9, and the readout circuitry 18 including the row-select shift register 32, column-select shift register 36, sample-and-hold circuits 54, analog switches 56, and wire bond pads 33. The preferred layout of the circuitry associated with an individual pixel 11 is shown in FIGS. 9 through 12. FIG. 9 is a top view of pixel circuit 11 showing the circuit elements in each layer superimposed on each other. FIGS. 10 through 12 show three different cross-sectional slices of the layout. Together, these figures show the locations of the electrode 14, capacitor 24, source-follower transistor 41, external selection line 53, selection transistor 30, column readout line 28, reset line 29, reset transistor 26, and ground line 27.

Selection transistor 30 and reset transistor 26 are n-channel transistors and are fabricated using an ion implantation process to add an electron-donor impurity, such as phosphorus, to specific regions 146 and 145 in the p-type substrate 7, as shown in FIG. 10, in order to form n-type source 146 and n-type drain 145 on both sides of p-type region 167 in substrate 7. N-type source 146 and drain 145 each form n-p diodes with p-type substrate 7. These diodes are intentionally reverse-biased with respect to substrate 7 or have no voltage across them, thus preventing current from flowing between source 146 and drain 145. Transistor gate 169, fabricated from an electrically conductive layer of polysilicon, is separated from p-type region 167 by insulating oxide layer 170. A positive voltage between gate 169 and substrate 7 causes an electric field in region 167 which repels p-type carriers (holes) and attracts n-type carriers (electrons) into region 167. This charge redistribution converts region 167 from p-type to n-type, presents a continuous path of conducting n-type material between source 146 and drain 145, and allows selection transistor 30 to conduct electricity. When voltage between gate 169 and substrate 7 is zero or negative, these transistors do not conduct.

Source 146 and drain 145 regions of each transistor are connected to other circuit components by either conductive layers of polysilicon or conductive metal layers of aluminum. FIG. 12 shows source 146 and drain 145 of reset transistor 26 connected to electrode 14 (which is connected to capacitor 24 by a line not shown) and ground line 27, respectively. A positive voltage on gate 169 of reset transistor 26 allows capacitor 24 to be drained to ground 27. FIG. 10 shows source 146 of selection transistor 30 connected to Col(out) line 28. Drain 145 of selection transistor 30 is connected to source 153 of source-follower transistor 41 through an electrical path not shown in FIG. 12. A positive voltage on gate 169 of selection transistor 30 allows Col(out) line 28 to be electrically connected to source 153 of source-follower transistor 41. Drain 155 of transistor 41 is connected to ground line 27.

FIG. 10 shows that source-follower transistor 41, a p-channel transistor, requires a substrate of n-type silicon which is provided by n-well 133. N-well 133 is an island of n-type material created in p-type silicon substrate 7 by an ion implantation process. N-well island 133 forms an n-p diode with substrate 7 and is kept at a positive voltage with respect to substrate 7 to electrically isolate n-well 133 from substrate 7. Source 157 and drain 159 of transistor 41 are formed in n-well 133 by ion implantation of an electron-acceptor impurity, such as boron, to convert source 157 and drain 159 into p-type silicon. Transistor gate 168, fabricated from an electrically conductive layer of polysilicon, is separated from n-type region 133 by insulating oxide layer 170. A negative voltage on gate 168 causes an electric field in region 153 which repels n-type carriers (electrons) and attracts p-type carriers (holes) into region 153. This charge redistribution converts region 153 from n-type to p-type, presenting a continuous path of conducting p-type material between source 157 and drain 153, and allows transistor 41 to conduct electricity. Source 157 of transistor 41 is supplied a constant current from transistor 110, located in sample-and-hold circuit 54, when selection transistor 30 is turned on. The magnitude of the voltage at gate 168 (which represents the charge collected by electrode 14 and stored on capacitor 24) of source-follower transistor 41 controls the conductivity of transistor 41; hence the source of transistor 41 follows the voltage on capacitor 24 except for an offset voltage of approximately 0.5 Volts.

The passive electrical circuit components are produced by adding alternate patterned layers of electrical insulators and conductors. Electrical insulating layer 156 is provided by boron-phosphorus-silicon glass. The insulating layers 176 and 180 are provided by silicon dioxide ($SiO_2$). Doped polysilicon provides the electrically conducting parallel plates 171 and 173 of capacitor 24, as well as reset line 29. Aluminum-copper metal provides the electrically conducting column readout line 28, external selection line 53, ground line 27, and electrode 14.

The readout circuitry 18 is fabricated in a similar manner as the pixel circuit 11. N-channel and p-channel transistors are fabricated in the silicon substrate 7. Passive components are added in layers over the transistors.

Our prototype electronic readout arrays 12 were fabricated at ORBIT Semiconductor, Sunnyvale, Calif. This small scale design was fabricated on the same wafer with a number of other company's circuit designs, which resulted in an inexpensive fabrication run. We received thirty identical die, each die containing one electronic readout array 12 (see FIG. 4). The arrays were bonded to a conventional 28-pin chip carrier and wire bond pads 33 on each array were connected to the pins of the chip carrier by a conventional wire bonding technique. The wire bond pads 33 and wires were selectively coated with epoxy to protect them, leaving the pixel array 9 and readout circuitry 18 uncovered.

The prototype arrays were coated with amorphous selenium films using a vapor deposition process. Selenium films were deposited in various thicknesses up to 300 microns over the entire electronic readout array 12, including the pixel array 9 and the readout circuit 18. A 300 micron thickness provides good results for absorption of x-rays in the spectrum utilized in mammography applications from 17 keV to 28 keV. A 300 micron thick layer of selenium absorbs substantially all of the incident x-rays and protects the electronic readout array 12 from x-ray induced damage. However, the selenium layer 10 is thin enough so that the voltage from source 16 required for a given electric field does not become unreasonably high. The breakdown field strength for selenium is approximately 20 V/micron. A safe field strength is 5 V/micron, equivalent to 1500 volts across a 300 micron thick layer 10 of selenium.

The prototype sensors were then coated with a conductive electrode 8 of silver using a vapor deposition process. The silver thickness of 250 angstroms allows transmission of over 99.9% of the incident x-ray photons in the range of 17 keV to 28 keV, and yet is thick enough to provide adequate electrical conductivity across its surface. The conductive electrode for each of the coated arrays was electrically connected to the chip carrier.

The prototype sensors were electrically connected to data acquisition electronics 20, which includes a circuit board to route power and clock lines to the sensor and to route output line 72 through an amplifier to a 12-bit analog-to-digital converter. A timing board generates the clocks required for the shift registers 32 and 36. The digital data from the analog-to-digital converter was sent to a 486 computer 23 which displays images 21 on monitor 22.

The prototype sensors were tested by directing x-rays 2 from a molydenum-anode x-ray source 4 through various targets 6 onto sensor 1. X-ray images acquired with one of these prototype sensors are displayed in FIGS. 13A and 14B. FIG. 13B is an x-ray image of a portion of a wire mesh screen 132 depicted in FIG. 13A. FIG. 14B is an x-ray image of a portion of the eye of a needle 136 depicted in FIG. 14A. Initial results indicate that our prototype sensors have a nominal response of approximately 50 electrons per x-ray photon and a nominal rms dark noise of approximately 400 electrons which translates to eight x-ray photons of dark noise.

CMOS TECHNOLOGY

An important embodiment of this invention is its use of complimentary metal oxide semiconductor fabrication technology. The CMOS technology offers very good performance with regard to speed, power consumption, and leakage currents; and it is very flexible since it allows the circuit designer to combine transistors of both p-type and n-type polarities on the same integrated circuit. CMOS allows both analog and digital circuits to be fabricated on the same piece of crystalline silicon, including not only the array 9 of pixel circuits 11 but virtually all of the readout electronics, including shift registers 44, sample-and-hold circuits 54, analog switches 56, and even analog-to-digital converters. Because CMOS is a very popular and mature technology, CMOS fabrication processes are relatively inexpensive and are readily available in many variations at most semiconductor foundries.

One of the available CMOS processes is an older process allowing minimum feature sizes of two microns. For this process the photolithographic masks with the circuit patterns are projected onto the entire surface of the substrate wafer of single-crystal silicon instead of onto smaller portions of the wafer, as with more modern processes capable of smaller feature sizes. Wafer diameters of four inches may presently be used with this process, and whole-wafer projection using six inch diameter wafers will soon be available. Thus, our prototype sensor array can be scaled up to provide much larger sensors as needed for various types of medical x-ray imaging.

This CMOS design is suitable for an n-well fabrication process. This specification refers to the ion implantation process used to create islands of doped silicon on the substrate. These islands have majority charge carriers opposite in type to the majority charge carriers of the substrate. Thus, an n-well process creates islands of n-type material in a substrate of p-type material. A p-well process creates p-type islands in an n-type silicon substrate. The difference in the circuits relates to whether the circuit voltages are positive or negative with respect to the substrate. For our first full scale device we used the n-well process in a p-doped wafer because our small prototype array is an n-well device and performs very well. However, we could also use an n-doped wafer with p-wells and our invention is intended to cover both approaches.

Circuit Defect Strategy

One object of this invention is to provide a large-scale sensor with a square or rectangular image format large enough to cover the majority of a four-inch or six-inch diameter silicon wafer. A preferred embodiment of this large-scale sensor 190, shown in FIGS. 15A and 15B, occupies an area of 46 square centimeters. The process yield is low for a normal CMOS design of this size, since the probability for serious defects is very high for large-area chips. These defects arise from unavoidable dust and dirt particles which find their way onto the surface of the masks or the wafer in spite of stringent cleanliness requirements.

Figure 15A:
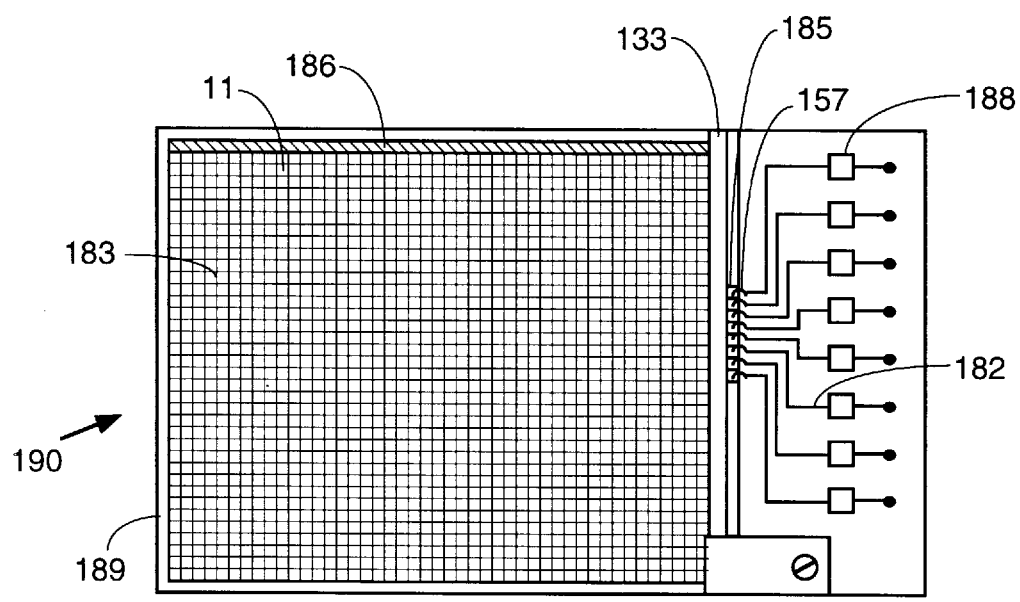
FIGS. 15A and 15B are drawings showing the principal elements of an image sensor presently being fabricated by the inventors.

The basis of the design strategy for the full-scale sensor is suggested by the observation that the area occupied by our integrated circuit can be divided into two regions of differing nature; one region is the very large area occupied by the pixel array 183, and the other region is the smaller region, less than one percent of the total, occupied by the readout circuits 133 and 186 at the edges of the array (see FIG. 15A). The occurrence of defects in the region of the readout circuits 133 and 186 will probably disable the entire integrated circuit. However, the probability for any defects in this region is quite small because the area of the region is small; and thus normal care in design such as keeping circuit features well separated and avoiding unnecessary or vulnerable components will be sufficient for this region. On the other hand, because the occurrence of defects in the large region of the pixel array 183 is almost certain, then we must accept their inevitability and take steps to minimize their effect on the performance of the device.

Circuit defects are of two main types: defects resulting in breaks in conducting lines, and defects causing electrical shorts between lines or components. In the pixel array 183 the effect of the first type of defect is limited to loss of function for the individual pixels 184 served by the defective feature, either one pixel or part of a row or column of pixels. However, the second type of defect in the pixel region can lead to loss of function for all of the pixels in the array if the short circuit causes large currents to flow in essential parts of the peripheral readout circuitry 133 and 186. Therefore, part of our strategy is to eliminate opportunities for catastrophic damage by adding buffer amplifiers 50 or resistors 51 (see FIG. 16) to most of the lines connecting the pixel region to the peripheral circuits in order to limit the current drain on the external circuits to tolerable levels in the event of a few short-circuit defects. For example, a defect which shorts out one of the reset lines to the grounded substrate would wipe out the entire reset capability of the readout circuitry if the circuit were designed with all the reset lines connected in parallel directly to a common bus. Therefore, we connect the reset bus 66 to the reset lines 29 through buffers 50 (FIG. 6) or resistors 51 (FIG. 16) to isolate the control circuitry on the edge of the array from problems downstream in the pixel region. For the same reason, the readout select lines 53 in the pixel region are isolated with buffers 50 from the select shift register 186 on the edge of the array. Otherwise, damage to one of the readout select lines in one of the pixels could disable the shift register controlling the entire readout process. There is a similar problem with providing a connection to a supply-voltage bus in each pixel, since a pixel defect shorting out the supply-voltage line could wipe out the supply voltage for all pixels. Therefore, the voltage used by the active elements in the pixels must be provided by some less direct means. The pixel circuits 11 do not have power supplied by a separate power supply line. Instead, the pixel power is provided through column output lines 28, which are connected to current source transistors 110 in the sample-and-hold circuits 54 (see FIG. 8) at the edge of the array.

In spite of our design strategy, the effect of defects is still a problem; defects cause loss of function in all pixels in some individual rows or columns and even destroy adjacent pairs of rows and columns, but the remaining pixels will still operate properly. Missing individual pixels and even missing rows or columns are corrected by having the computer 23 assign values to the missing pixels by interpolation between the values of the neighboring pixels, and very little diagnostic value is lost. A more accurate method of dealing with defective pixels involves the use of two exposures in succession with a small diagonal shift of the entire sensor 190 of 10 to 20 pixels between the two exposures. The computer 23 then combines the two exposures into a single image and the single image will have very few missing pixels. For further accuracy, this method can be extended to three successive exposures with diagonal shifts of the sensor 190 between each exposure.

The use of three successive exposures with the small diagonal shift also helps with the problem of combining a number of these sensors into a full format sensor. The full format sensor has gaps which are non-responsive to x-rays between the individual sensors. The triple-exposure technique corrects missing rows or columns, and it also permits us to fill in the gaps with x-ray information between the individual sensors. Another benefit of the triple-exposure technique is that it permits the construction of a more efficient device for x-ray scatter rejection, as explained below.

832×1024 PIXEL IMAGE SENSOR

Figure 15B:
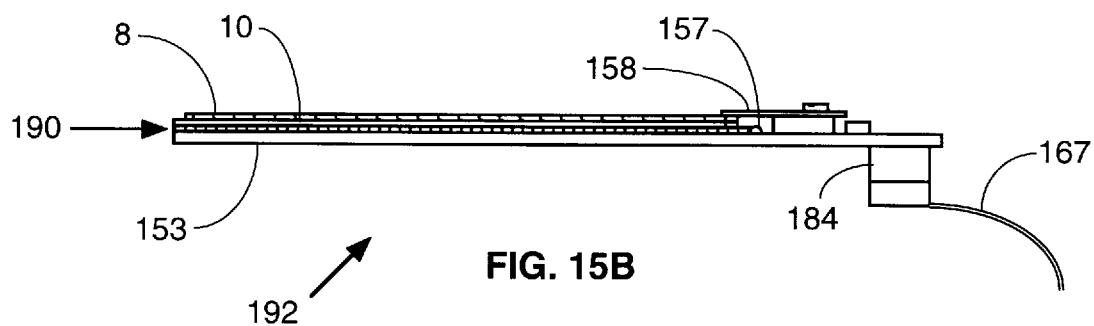

The second preferred embodiment of the invention, shown in FIGS. 15A, and 15B, provides an electronic readout array 190 with a 832×1024 pixel array 183 of pixel circuits 11, and readout circuitry 133. This embodiment has been fabricated and tested by the inventors and their fellow workers. The size of each pixel circuit 11 is 66 microns×66 microns resulting in an image format of 5.5 cm×6.75 cm. An outline drawing of readout array 190, as in our prototype, is shown in FIG. 15. Row-select shift register 186 occupies a width of approximately 100 microns (less than two pixels) and extends along the entire length of one edge of the pixel array 183. The electronic readout circuit 190 has a very thin (less than 250 micron) edge 189 around three of the sides. The readout circuitry 133 requires a relatively small area, approximately 0.1 cm×6.75 cm, and wire bond pads 185 are provided at this edge to make control, output, and power connections.

Figure 16:
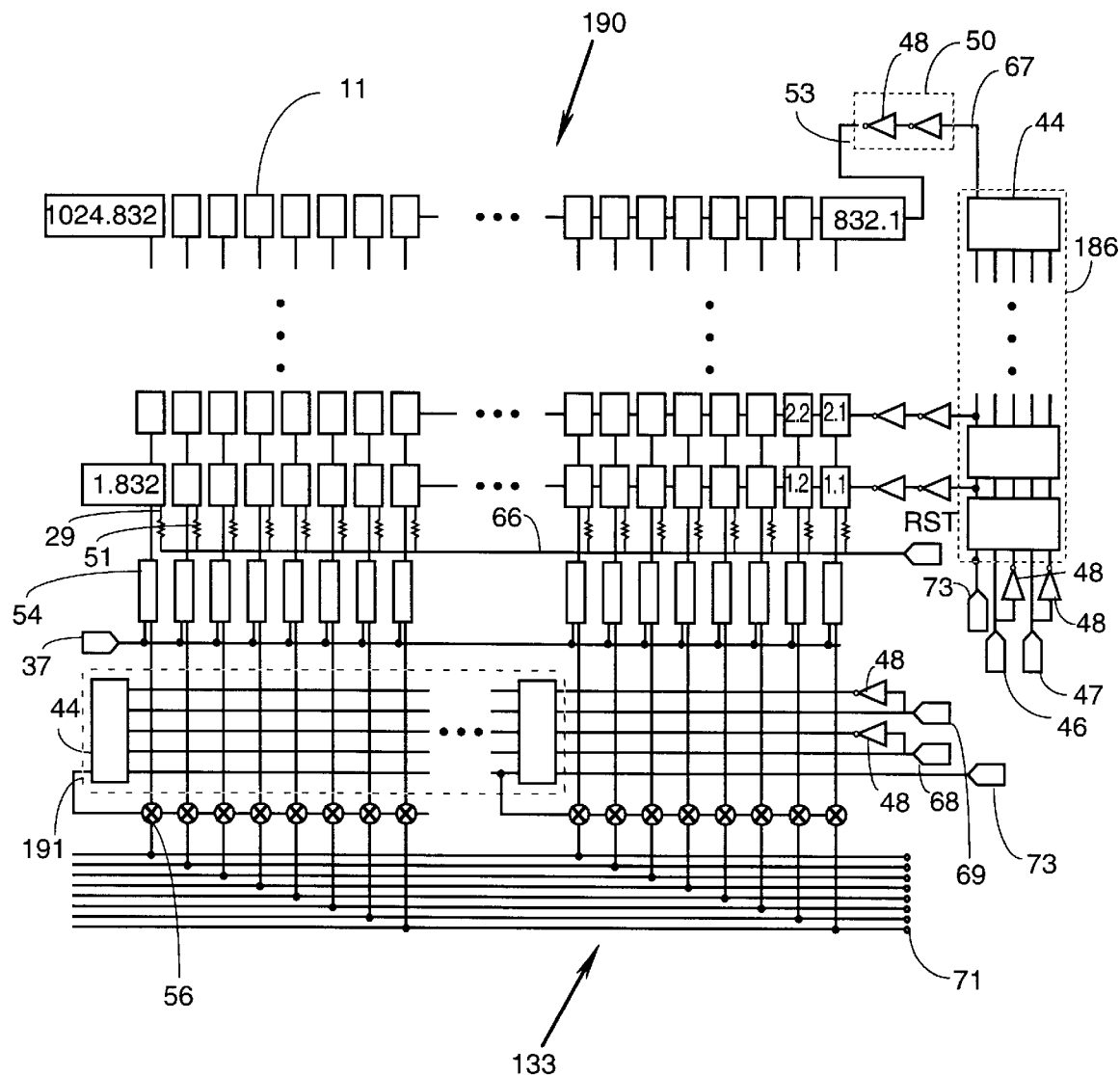
FIG. 16 is a schematic diagram of the electronic readout array in the second preferred embodiment.

FIG. 16 shows a schematic diagram of the electronic readout array 190. Row-select shift register 186 contains 832 flip-flops 44, one for each row, and controls the row selection for readout purposes. Readout circuit 133 contains a sample-and-hold circuit 54 and a bilateral switch 56 for each of the 1024 columns of pixel circuits 11. The column-select shift register 191 contains 104 flip-flops 44, one for each set of eight columns. The output from each flip-flop 44 output controls eight bilateral switches 56 which simultaneously connect groups of eight outputs of sample-and-hold circuits 54 to eight parallel output lines 71. Voltages from output lines 71 are buffered and routed to data acquisition electronics 20. The circuit diagrams of the flip-flop 44, and sample-and-hold circuits 54 are shown in FIGS. 7 and 8, respectively.

The eight separate outputs provide some important benefits. We have provided for a 125 milliseconds readout time for the entire array. This requires a data rate of 8 MHz for one million pixels if we have only one output line. This high data rate requires the output driver to supply large currents needed to rapidly charge and discharge the parasitic capacitance of the output line 71. The large currents require a wide output line 71 running the length of the edge of the readout circuitry 133, which increases the parasitic capacitance of the output line 71. The incorporation of eight parallel output lines 71 running at one eighth of the total data rate reduces the current and therefore the width of each line 71. The particular configuration for the eight outputs shown in FIG. 14 results in a simple topography for the network of crossing lines and also facilitates pixel readout in a normal raster scan sequence with a fast eight-to-one analog multiplexer and a fast analog-to-digital converter in the data acquisition circuitry 20 external to the electronic readout array 190. If instead the readout scheme were not sequential along each row, then the normal cross-talk inherent in fast analog-to-digital converter circuits would be between non-neighboring pixels and would result in noticeable ghost images.

The reset circuitry shown in FIG. 16, is similar to the reset circuitry of the small-scale prototype array, except that the reset buffers 50 shown in FIG. 5 are replaced with polysilicon resistors 51. This change allows the option of turning off the reset transistors 26 with a reversed gate-to-source voltage (−2 Volts for this embodiment) in order to avoid leakage of charge through the reset transistors 26.

Each electronic readout array 190 is fabricated on a four-inch diameter wafer of crystalline silicon 7, using the CMOS fabrication methods previously described. In order to facilitate close butting of the arrays, each wafer is then cut with a diamond saw to provide narrow border regions 189 on the three sides without the readout circuitry 133 and wire bond pads 185.

Readout array 190 is coated with amorphous selenium 10. For the preferred embodiment of the invention utilized for the mammography application, the selenium is evaporated at 80° C. onto the readout array 190 as a 300 micron thick amorphous coating. The selenium is alloyed with 0.3% arsenic to prevent recrystallization of the amorphous selenium. A trace amount of chlorine (12 ppm) is added to the alloy in order to passivate hole traps in the selenium/arsenic alloy. The selenium-coated readout array 190 is then coated with a conductive electrode 8. The preferred electrode is a 12 micron thick layer of graphite impregnated paint (Aquadag, Acheson Colloids). This electrode is reasonably sturdy, high transmissive to x-rays, sufficiently conductive and can be applied at room temperature.

Electronic readout array 190 is attached to a chip carrier 153, as shown in FIG. 15B, which is fabricated from an electrically insulating, thermally stable material such as aluminum oxide ($Al_2O_3$) or FR4 printed circuit board material. Chip carrier 153 is fabricated with electrically conductive routing lines 182, and electrical connections from readout array 190 to lines 182 are made with wire bonds 157. Readout array 190 is coated with amorphous selenium 10 and then with a conductive electrode 8 before attaching to chip carrier 153. The eight analog output lines 71 from readout array 190 are routed via lines 182 to transistor buffer amplifiers 188 which send amplified analog signals to ribbon cable 167 via connector 184. Ribbon cable 167 routs signal to external circuitry which amplifies the voltages from output lines 71 and converts the analog voltages to digital data via analog-to-digital converters. Ribbon cable 167 is also used to route clock and control circuitry to supply clock and data signals to shift registers 191 and 186, control signals for the sample-and-hold circuits and the reset function, digital transmission circuitry to transmit the digital data to computer 23, and power circuitry to supply electrical power to the readout array 190. Chip carrier 153 is approximately the same size as the electronic readout array 190 in order to facilitate butting of the image sensors to form a full format image sensor.

Figure 26:
FIG. 26 is a digital printout of an x-ray image of a mouse made with a preferred embodiment of the present invention.

FIG. 26 is a digital printout of an x-ray image of a mouse made with one of our 832×1024 pixel image sensors.

FULL FORMAT IMAGE SENSOR FOR DIGITAL MAMMOGRAPHY

One object of this invention is to provide a high-resolution digital x-ray image sensor large enough to image large areas of the human body, such as the full breast, for example. The two standard film sizes for film/screen mammography, 18 cm×24 cm and 24 cm×32 cm, approximate the preferred size for a full-format digital sensor for the mammography application. Current CMOS processing technology constrains the maximum size of a monolithic digital sensor to 5.5 cm×6.75 cm for a four inch diameter wafer (or 10.1 cm×10.1 cm for a six inch diameter wafer). This size constraint necessitates combining a plurality of these smaller image format sensors to form a full format sensor.

Figure 17A:
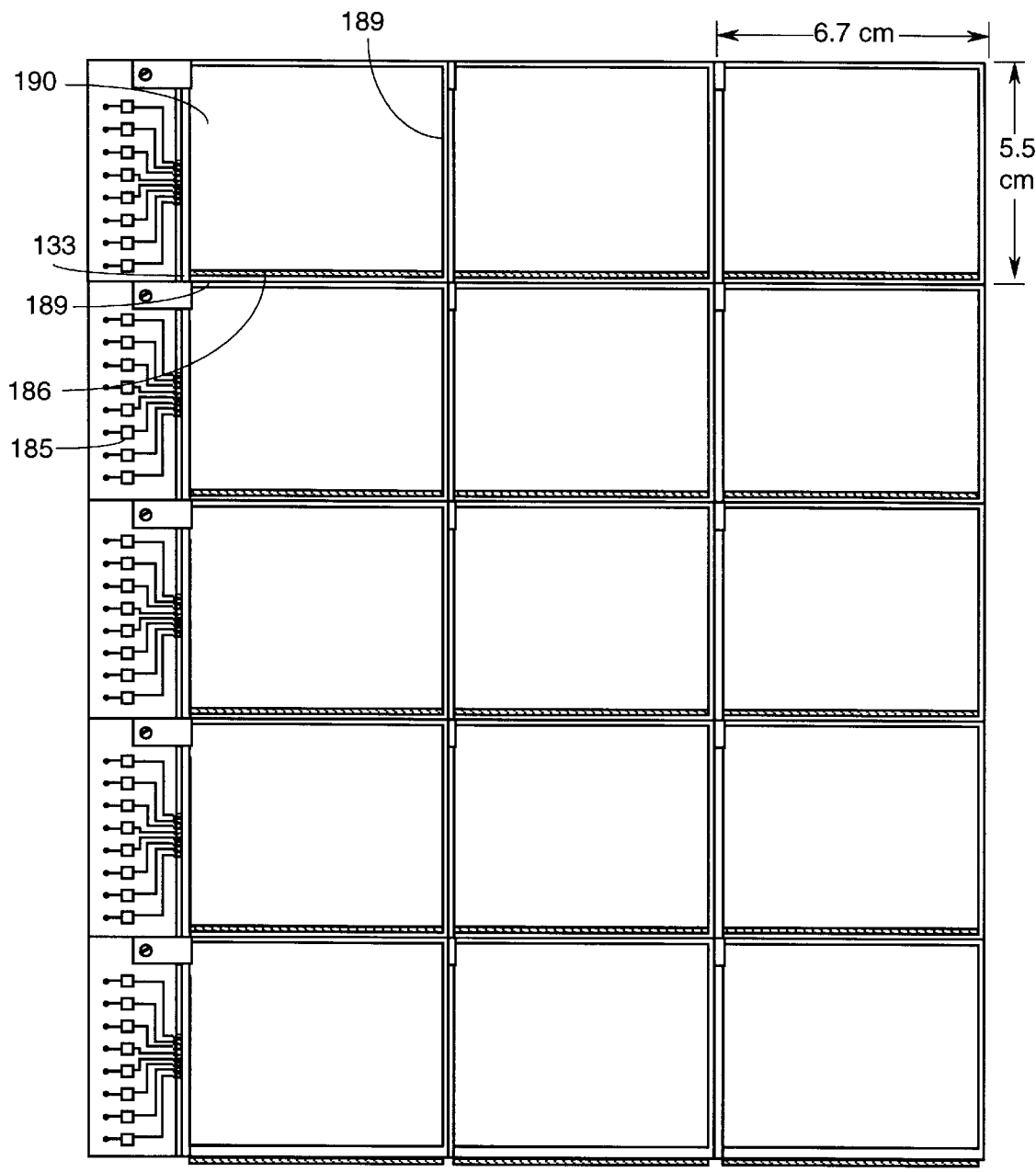
FIGS. 17A and 17B are diagrams showing a method for combining multiple image sensors in order to produce a larger format imaging sensor.
Figure 17B:
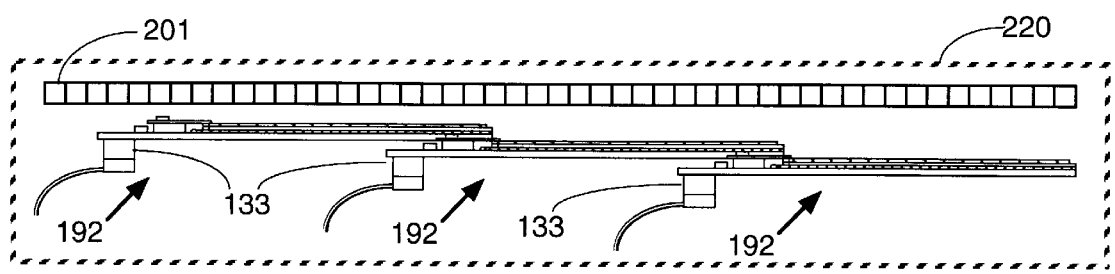

FIGS. 17A and 17B show a preferred approach for fabricating a full-format image sensor. Fifteen of the 832× 1024 pixel image sensor assemblies 192 are combined in a 3×5 array to produce an image area of 20 cm×27 cm containing 12.8 million pixels in a 3072×4160 pixel array. We first butt five image sensor assemblies 192 together in a row. We then shingle three of these sensor rows together with the readout circuitry 133 and wire bond pads 185 of each successive row lying underneath the previous row as shown in FIG. 17B. The eight analog signals from each of the fifteen image sensor assemblies 192 are routed through ribbon cables 167 to a custom data acquisition board. This board features two 4-to-1 analog multiplexers and two 12-bit analog-to-digital converters for each sensor assembly 192. The multiplexed analog signals are modified using software programmable voltage gain and offset amplifiers in order to optimize the input of the analog-to-digital converters. The 12-bit digital signals from the 30 analog-to-digital converters are routed via ribbon cables to a custom digital acquisition board which features 8 Mbytes of random access memory (RAM) for each of the image sensor assemblies 192, thus allowing digital storage of four images. The digital data from the RAM is then serially transmitted via a TAXI transmitter to a custom TAXI/PCI interface board residing in a computer system 23 which preferably is a Pentium-based system or equivalent. The images are processed and displayed on computer monitor 22 or printed on a high-resolution laser film printer. The full format image sensor 194 shown in FIGS. 17A and 17B, has gaps 186 and 189 between adjacent image sensors 192 which are non-responsive to x-rays.

Figure 18:
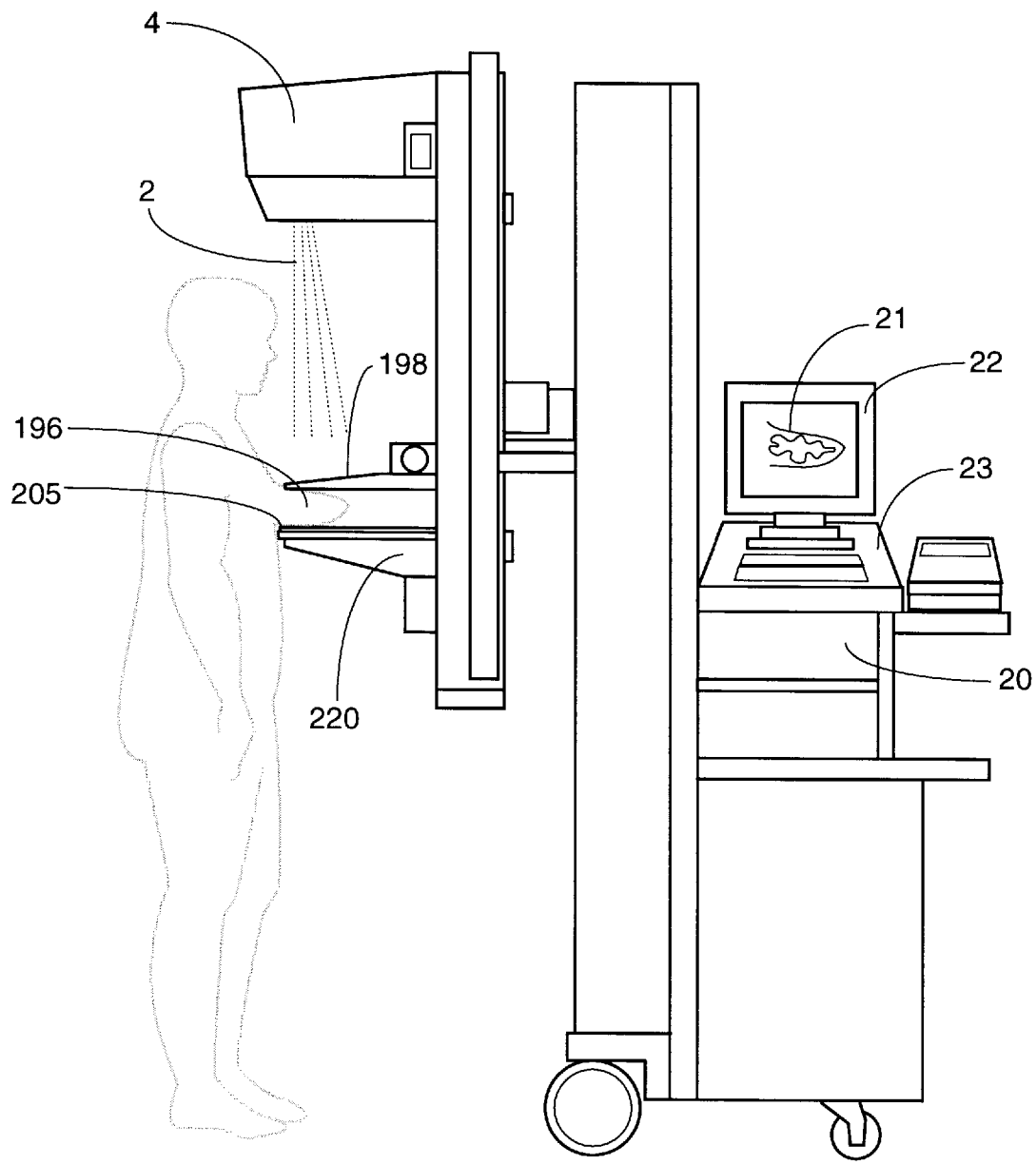
FIG. 18 is a diagram showing the invention used in the mammography application.

FIG. 18 shows our full format image sensor incorporated in a digital x-ray mammography device. This device includes sensor/grid assembly 220 shown in FIG. 17B which incorporates the full format digital image sensor 194 and x-ray anti-scatter grid 201 described below. X-ray source 4 directs x-rays 2 through breast 196 which is compressed between compression paddle 198 and breast tray 205. The x-rays 2 pass through breast tray 205 to the assembly 220. Image data is acquired with data acquisition electronics 20 which converts the data to digital form and transmits the digital data to computer 23 which processes the data to produce image 21 on computer monitor 22.

Anti-Scatter Grid

For most x-ray imaging situations, a large amount of radiation scatters from the object being imaged. These scattered x-rays contain no usable imaging information but can have an intensity equal to or greater than the unscattered primary radiation containing the image information. If this scattered radiation is allowed to reach the imaging sensor, it will not only fog the image and reduce the contrast but, because of the random statistical nature of the x-ray production, absorption, and scattering processes, the scattered radiation will also add random fluctuations on top of the normal random fluctuations contained in the image-bearing primary x-rays. The signal-to-noise ratio can be degraded to such an extent that it is necessary to increase the x-ray dose to the patient 100% or more in order to compensate for the degradation.

For medical screen/film images the scatter is usually reduced by means of the x-ray grid or Buckey, a device stationed below the scattering object and composed of multiple x-ray absorbing slats oriented to allow passage of only those rays on paths consistent with emanation from the x-ray source and stopping those rays with directions altered by angular scattering. This grid introduces serious problems of its own: the pattern of the grid can appear on the image, and the grid blocks or absorbs a substantial portion of the primary beam. The usual solution to the problem is to use very fine and very expensive grids built up of many alternate layers of low-absorption and high-absorption materials with the layer planes angled toward the location of the x-ray source. For low-resolution requirements, such as chest x-rays, these grids are usually stationary; and for high-resolution requirements, such as for mammography, the grids are moved during the exposure to reduce the imaging of the grid. Design trade-offs for optimizing these grids for various applications result in specialized combinations of slat spacing, thickness, and width to achieve a performance compromise involving incomplete scatter cleanup in exchange for less loss of the primary beam. This loss of the primary beam can be as much as 50% and often nullifies most of the signal-to-noise benefit of the scatter reduction.

A preferred embodiment of our invention includes an anti-scatter grid designed to take advantage of opportunities presented by features of the present invention. The grid consists of an array of tantalum or tungsten ribbons 0.002 inch thick by 1 inch wide and spaced by 0.2 inches. These ribbons are stretched on a frame holding the ribbons planes parallel to the primary x-rays. This grid would block most of the scattered radiation but could, for very flat and accurately-angled ribbons, block only 1% of the primary x-rays. Instead of providing independent motion of the grid assembly in order to reduce the imaging of the grid, this grid assembly is fixed to the x-ray sensor stationed just below the grid assembly. The pixels blocked by the grid ribbons are treated as missing pixels, and these missing pixels are filled in with the technique of the triple exposure with a diagonal shift in the same manner as the pixels missing in the gaps between the butted arrays and in the defect-damaged rows and columns. Thus we have a means of providing an inexpensive anti-scatter grid having nearly ideal performance.

IMAGE ACQUISITION AND PROCESSING

Initializing Electronics and Software

Embodiments of the present invention are initially characterized to identify hardware imperfections including dead or weakly responding pixels in each sensor 192, gaps between the different image sensors 192, spatially varying illumination of the x-ray source 4, and gain variations of the pixels 11. The characterization information of the hardware imperfections is used to process the breast image data produced by the mammography system in order to maximize the final image quality.

The preferred characterization procedure requires the acquisition of eight dark field images with the x-ray source 4 turned off and eight white field images, acquired with a 2 cm thick sheet of Lucite on the breast tray 205 and illuminating the full format sensor 194 with x-ray source 4. A dark field image is subtracted from a white field image to produce a residual frame and eight of these residual frames are averaged to form one calibration frame. Dead or weakly responding pixels in each sensor 192, and gaps between the different sensors 192, defined as having greater than 15% variation in luminance, are identified as defective pixels in the calibration image. Defective pixels are corrected in the calibration image by interpolation of eight nearest neighbors for point defects and six nearest neighbors for column or row defects. The calibration image is then stored in the computer 23 as an array of pixel values and the positions of each defective pixel are stored as a defect map. We also average the pixel values in the calibration image and store this single mean value. For this preferred embodiment, there are up to 12,779,520 (3072×4160) pixel values.

Image Data Acquisition

The preferred x-ray source 4 for the mammography application is a molybdenum-anode x-ray tube with a 50 micron thick molybdenum filter, which produces an x-ray primarily consisting of two sharp spectral lines at 17.9 keV and 19.5 keV. A second preferred source 4 for the mammography application is a tungsten-anode x-ray tube with a 50 micron thick silver filter, which produces an x-ray spectrum centered around 26 keV. The typical x-ray dose for the mammography application is 200 millirads (mean glandular dose) per image.

A preferred procedure for obtaining a mammogram is as follows: two x-ray images of the breast 196 are sequentially acquired. The first image is acquired using one half of the x-ray dose presently used for film/screen mammography. This image has a number of gaps 186 and 189 between sensors 192, pixel columns and rows which are shadowed by x-ray grid 201, and dead pixels in each sensor 190. The entire assembly 220, comprised of full format sensor 194 and x-ray grid 201 is moved to a second position which is displaced by twenty pixels in the x-direction and by twenty pixels in the y-direction from the first position. A second image is acquired with sensor/grid assembly 220 at the second position using the same x-ray dose as used for the first image.

For more accurate imaging the preceding procedure can be extended to three images as follows: Three raw x-ray images of the breast 196 are sequentially acquired. The first image is acquired using one third of the x-ray dose presently used for film/screen mammography. This image has a number of gaps 186 and 189 between sensors 192, pixel columns and rows which are shadowed by x-ray grid 201, and dead pixels in each sensor 190. The entire assembly 220, comprised of full format sensor 194 and x-ray grid 201 is moved to a second position which is displaced twenty pixels in the positive x-direction and by twenty pixels in the positive y-direction from the first position. A second image is acquired with sensor/grid assembly 220 at the second position, using the same x-ray dose as used for the first image. The entire assembly 220 is moved to a third position which is displaced by twenty pixels in the positive x-direction and by twenty pixels in the positive y-direction from the second position. A third image is acquired with sensor/grid assembly 220 at the third position, using the same x-ray dose as used in the first image. The three images are stored in computer 23. A single dark image (an "image" with no x-rays) with the same integration time as each of the three images is also acquired and stored to be used later to subtract electronic noise.

Producing Images from Image Data

The three images are corrected for gain variations of the sensor pixels and spatial variations of the x-ray source 4 by a procedure commonly known as "flat fielding." The value for each pixel in the corrected image is obtained by subtracting the dark image pixel value from the corresponding pixel in the calibration image, and then by multiplying by the calibration image mean value.

The three corrected images exhibit a slight difference in the average pixel values due to slight variations in the x-ray exposure. To correct for this effect, we normalize images 2 and 3 to image 1 by multiplying all the pixel values in the second corrected image by the ratio of the mean values of the first and second images and the first and third images. All known defective pixels and pixels obscured by the grid slats are assigned values of zero in the pixel-value arrays, and both arrays are given extra zero-value pixels to fill in the gaps between the sensors 194. Then the three pixel-value arrays are shifted (in the computer 23) relative to each other to account for the mechanical shifting of the sensor/grid assembly 220 between x-ray exposures and are summed pixel-by-pixel to form a composite image. Whenever a zero-value dead or defective pixel is added to two good pixel values, the value of the good pixels are multiplied by 1.5 to correct for the missing contribution to the sum. When two pixel values forming the sum are zero, then the remaining good pixel value is multiplied by three. The resulting composite image will show no lines representing the grid or the gaps between the sensors.

Image Enhancement

The final composite image of the full breast 196 is processed in the computer 23 in order to optimize the contrast between features in the breast. The preferred image enhancement procedure involves a preferential enhancement of the fine detail in the image while preserving the large-area contrast. The enhancement procedure calculates the natural logarithm transform of the pixel values of the image to reduce the contrast differences. The image, an enhancement procedure called "unsharp masking" is then applied to the image. This procedure is described in Section 7.4 of "Fundamentals of Digital Image Processing", by Anil K. Jain, Prentice Hall, N.J., 1989 which is incorporated herein by reference.

In addition, while viewing the image, the radiologist is able to adjust the parameters controlling the overall contrast in order to selectively enhance the visibility of features in different portions of the image.

FLUOROSCOPY IMAGE SENSOR

Another embodiment of the present invention provides a digital x-ray image sensor for fluoroscopy applications. Conventional fluoroscopy imaging devices include a variable repetition rate (7 to 90 frames per second) x-ray source and image sensor in order to record motion picture images of x-ray attenuation through various parts of the human body. These imaging devices are typically used for monitoring catheter placement for balloon angioplasty; monitoring the ingestion or injection of contrast agents, such as barium, for inspection of the digestive tract or blood vessels; and inspection of the beating heart. The conventional image sensor in these devices includes an image intensifier (II) tube which converts each incident x-ray photon into a plurality of electrons which travel through a vacuum and impinge on a scintillator. The scintillator converts each incident electron into a plurality of visible light photons which are then imaged with a visible image sensor, such as a charge-coupled device (CCD), for example. The visible light image from the CCD is viewed on a monitor, or recorded on film.

Figure 20A:
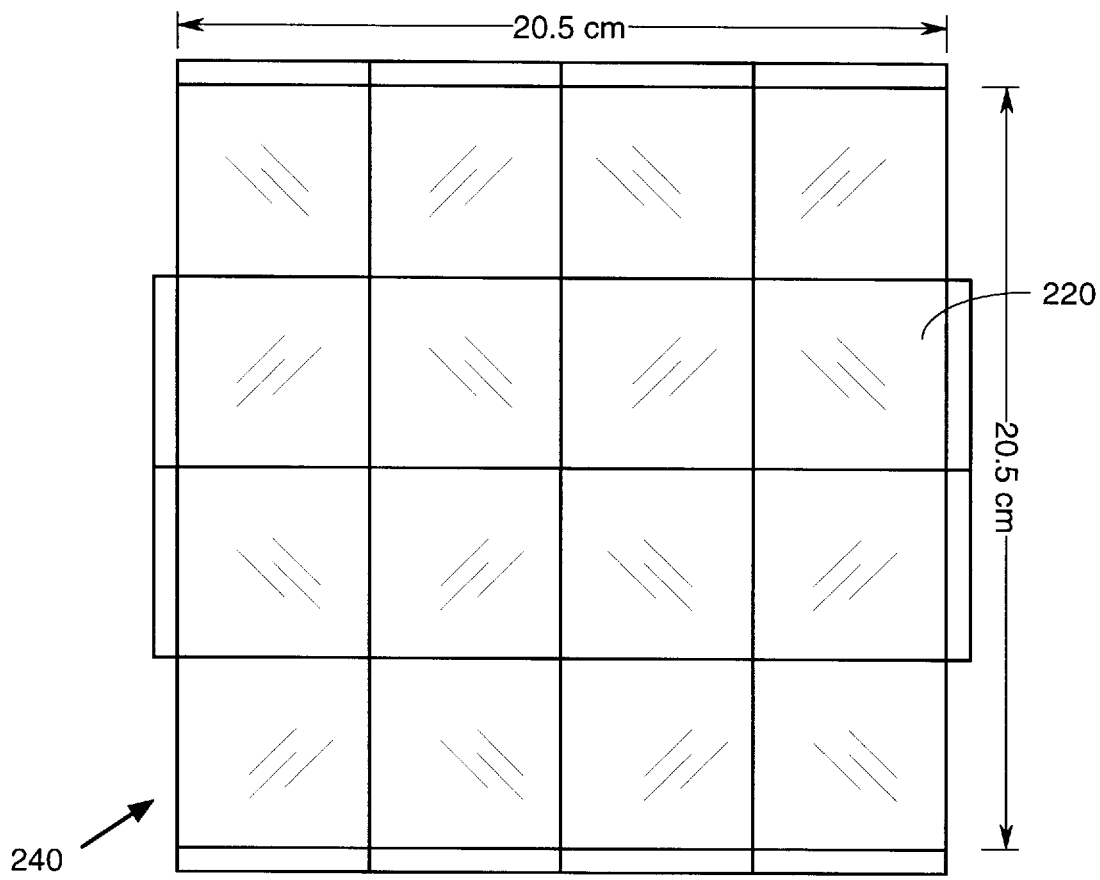
FIGS. 20A and 20B are diagrams showing a method for combining multiple image sensors in order to form a larger format image sensor.
Figure 20B:
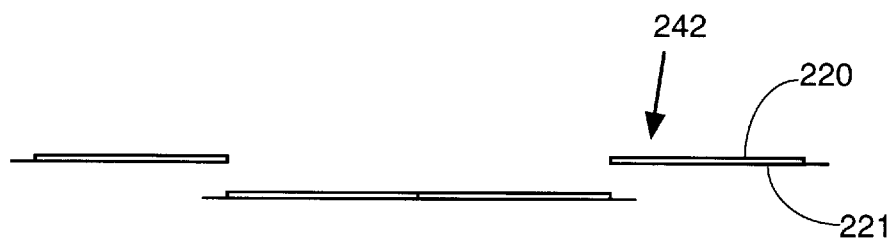

A fluoroscopy embodiment of the present invention is intended as a direct replacement of the image sensor in a fluoroscopy imaging device. The preferred embodiment of the fluoroscopy image sensor 240, displayed in FIGS. 20A and 20B, features a 1024×1024 pixel array with 200 micron pixels. The imaging area of this image sensor is 20.5 cm×20.5 cm. The image sensor is fabricated from sixteen smaller sensor subassemblies 242, each featuring a 256×256 pixel array of 200 micron pixels in a 5.12 cm×5.12 cm image format. The sixteen sensor subassemblies 242 are arranged in a 4×4 sensor array whereby twelve of the sensor subassemblies 242 are butted together to form the periphery of the image sensor 240. The remaining four image sensors 242 are butted together in a different plane to form the center section of the image sensor 240.

Fluoroscopy Sensor Circuitry

The fluoroscopy image sensor assembly 242 is substantially similar to the digital mammography image sensor assembly 192, displayed in FIGS. 15A and 15B. Electronic readout array 220, fabricated on a crystalline silicon wafer, is attached to a chip carrier 221. Readout array 220 is coated with selenium and a conductive electrode. The primary differences between readout array 190 are readout array 220 features larger (200 micron) pixels, a 256×256 array of pixels, a p-well CMOS circuit design to provide hardness to x-ray radiation, current mode output from each sample-and-hold circuit for shorter readout times, and two current outputs.

Figure 21:
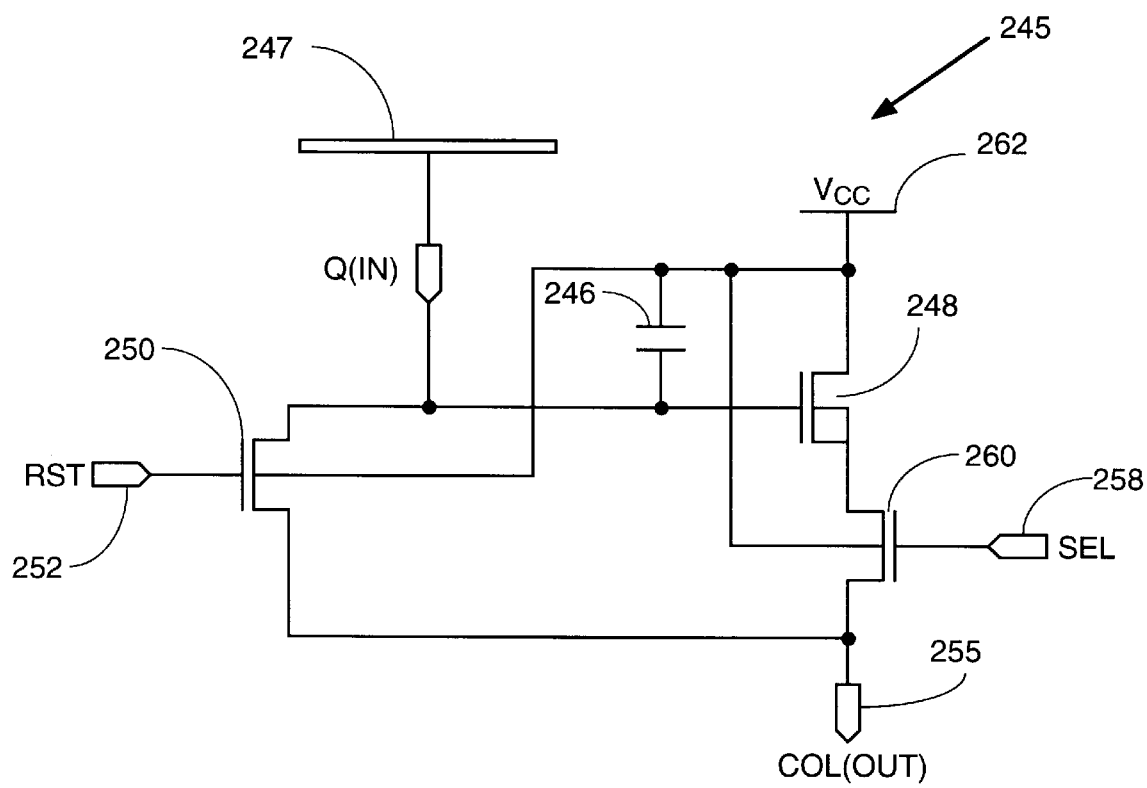
FIG. 21 is a circuit diagram of the elements in an individual pixel of the pixel array of a fluoroscopy prototype readout array.

The circuit diagram of the individual pixel circuit 245, displayed in FIG. 21, is similar to pixel circuit 11, displayed in FIG. 5. Pixel circuit 245 includes a collection electrode 247, collection capacitor 246, source-follower buffer 248, selection transistor 260, and reset transistor 250. The main difference between pixel circuit 245 and pixel circuit 11 is a reversal of the polarity. Pixel circuit 245 uses p-channel transistors for selection transistor 248 and reset transistor 250 and an n-channel transistor for source-follower transistor 248. The voltage at COL(out) 255 is inversely proportional to the collected positive charge Q(in). Pixel circuit 245 is referenced to a positive voltage Vcc at node 262 (typically 6 to 10 Volts) whereas pixel circuit 11 is referenced to ground 27. Pixel circuit 245 is designed to fit in a much larger 200×200 micron pixel area. Pixel circuit 245 is designed to enable a user-selected voltage VRST to be placed on capacitor 246 during reset. Voltage VRST is applied using line 255, which is also used at a different time to read the voltage COL(out) on pixel capacitor 246.

Figure 22:
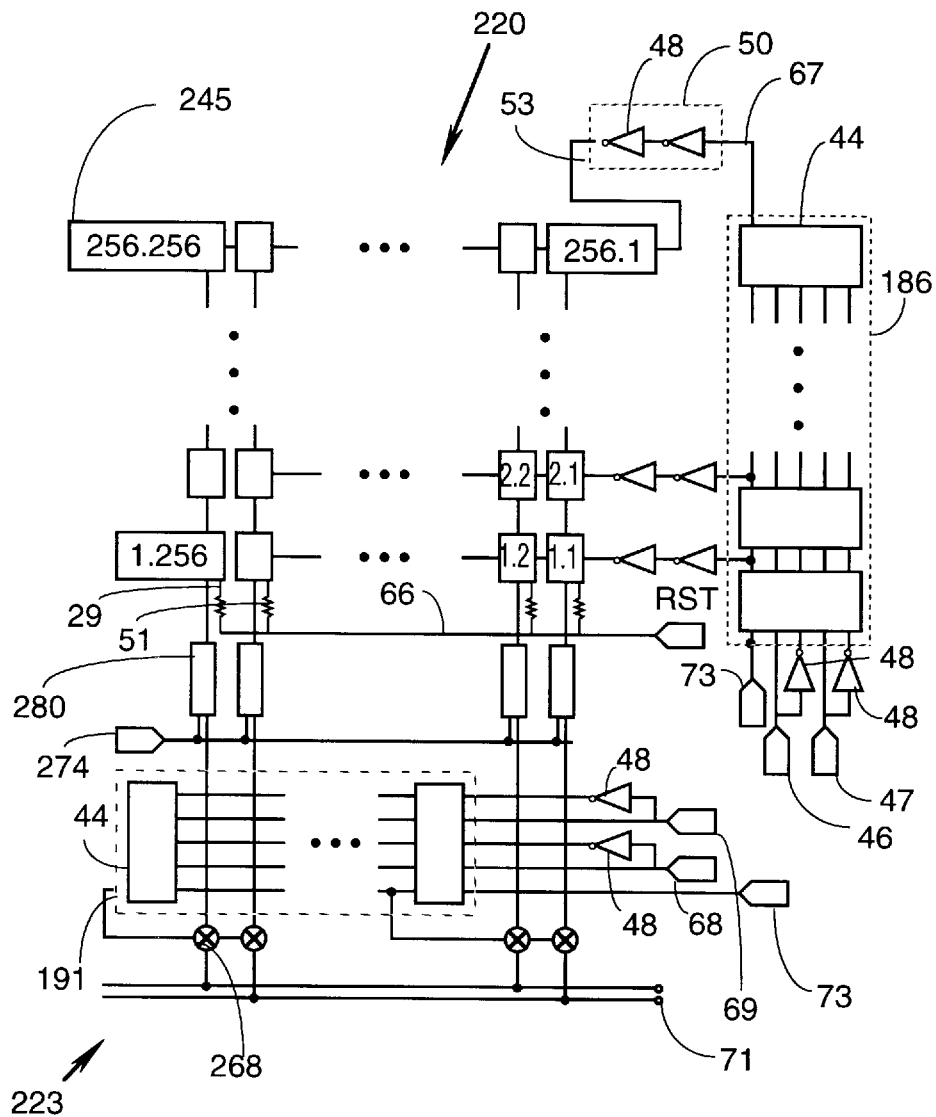
FIG. 22 is a schematic diagram of the electronic readout array utilized in the fluoroscopy embodiment.

The electronic readout circuit for the fluoroscopy sensor 220 displayed in FIG. 22 is substantially similar to the electronic readout array 12 described above with reference to FIG. 16 and FIGS. 5 through 8. Electronic readout array 220 features a 256×256 array of pixel circuits 245. Each row of pixel circuits 245 is sequentially selected by row-select shift register 186. A row of 256 sample-and-hold circuits 280 samples the voltage present at each pixel output COL(out) 255 and converts this voltage into a current which is proportional to the input voltage. The current output of each sample-and-hold circuit 280 is sequentially routed to two current outputs 272 through 256 analog multiplexers 56, controlled by 128 cells 44 of column-select shift register 191.

Figure 8A:
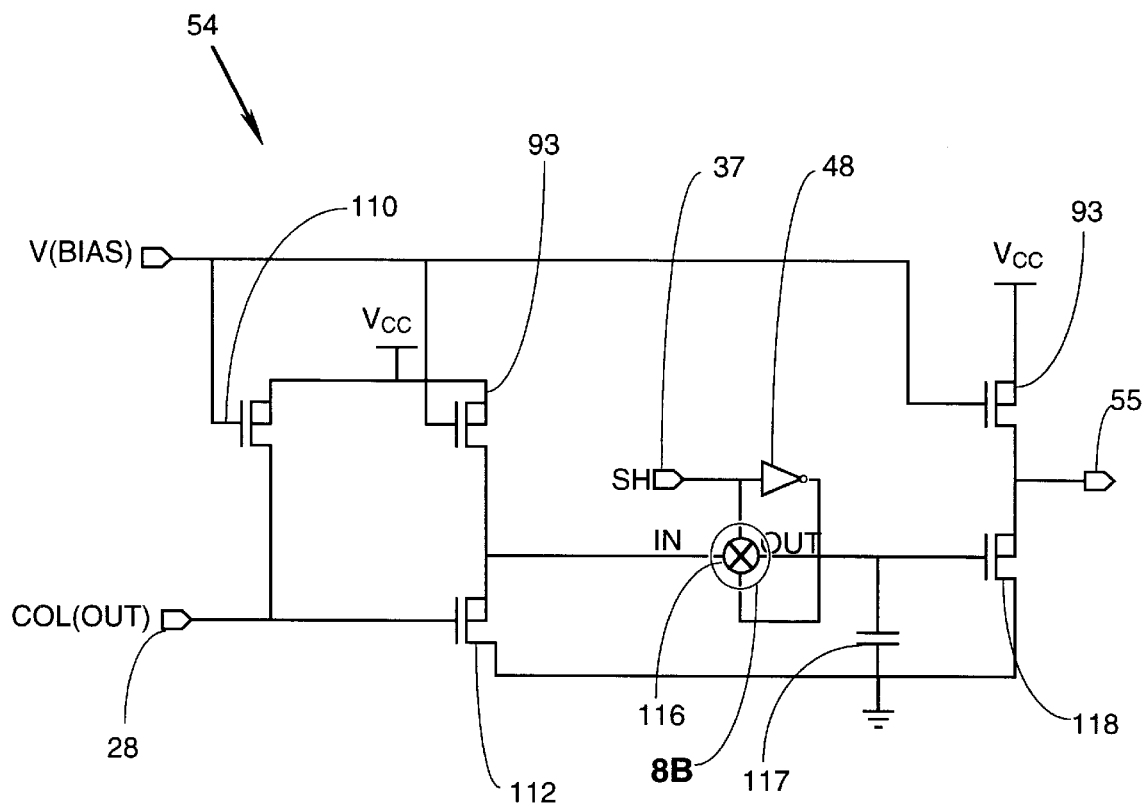
FIGS. 8A and 8B are circuit diagrams describing the sample-and-hold circuit used in the readout circuitry.
Figure 8B:
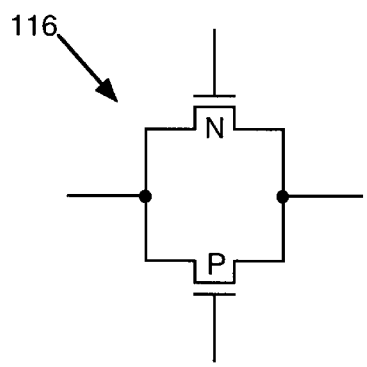
Figure 23A:
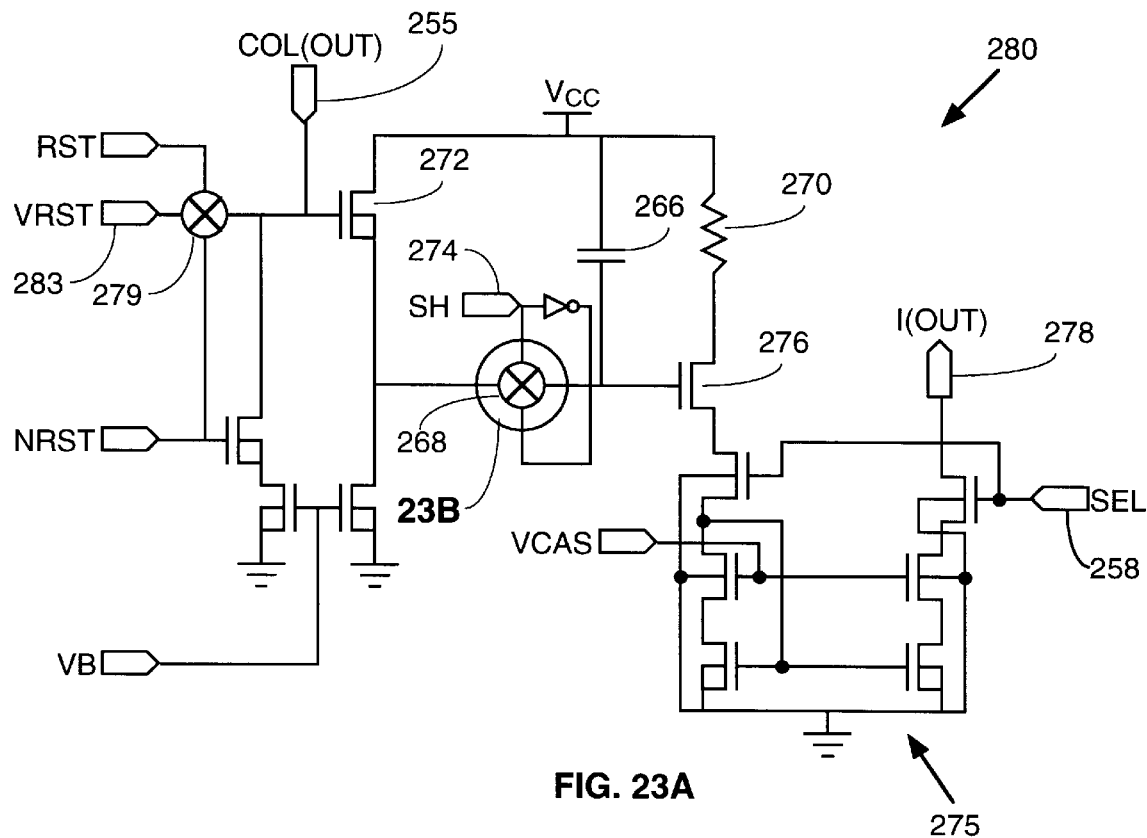
FIGS. 23A and 23B are circuit diagrams describing the sample-and-hold circuit used in the readout circuitry of the fluoroscopy prototype readout array.
Figure 23B:
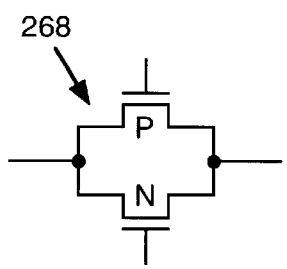

Sample-and-hold circuit 280, displayed in FIGS. 23A and 23B, is similar to sample-and-hold circuit 54, displayed in FIGS. 8A and 8B. The differences are that circuit 280 has a current output whereas circuit 54 has a voltage output; and circuit 280 has switches to allow either a user-selected voltage to be placed on line 255 or for voltage COL(out) to be sampled by circuit 280. When a row of pixel circuits 245 is selected by shift register 186, selection transistors 260 in all pixels in the row are turned on to connect the input 255 of each sample-and-hold circuit 280 with the source-follower transistor 248 at each pixel. Source-follower transistor 272 buffers the voltage on input 255 and presents this voltage to the input of bilateral analog switch 268. Analog switch 268, which allows current to flow in either direction when turned on by digital control signal SH 274, places the buffered voltage onto the 7.5 pF capacitor 266. The voltage on capacitor 266 is converted to a current by source-follower transistor 276 in series with 30 kohm resistor 270. This current is reproduced at output 278 by the current mirror circuit 275, which can be turned on and off by SEL input 258. Bilateral switch 279 is used to connect lines 255 to a specified reset voltage on line VRST 283 during the reset process. Otherwise the lines 255 are used to sample voltage COL(out) on line 255.

Radiation Damage Design Issues

The flexibility of CMOS design allows for radiation hardened design considerations. A predominant effect of x-ray and gamma radiation damage in metal-oxide semiconductor (MOS) circuits involves the liberation of electron/hole pairs in the $SiO_2$ layer which insulates the transistor gates from the conducting channels of the transistors. Electrons are swept out of the insulator layer by the externally applied bias field, while the holes, which have much lower mobility, become trapped in the oxide layer, and influence the field in the channel of the transistor. For n-channel transistors, most of the liberated holes are trapped at the oxide-silicon interface just above the conducting channel and tend to turn on the transistor. The threshold gate voltage required to form the conducting channel is reduced as irradiation effects accumulate until the transistor cannot be turned off (typically a 0.6 Volt usable range). For p-channel devices, the threshold gate voltage required to form the conducting channel is increased by x-ray irradiation. The increase in threshold voltage in p-channel transistors is not as serious as the threshold reduction in n-channel transistors, since there is more usable range, as much as 6 Volts, in the direction of larger threshold voltage values. In addition, for the p-channel transistors the holes are trapped near the metal gate, on the opposite side of the insulator, remote from the conducting channel; thus the magnitude of the effect is reduced compared to an n-channel device.

The design of electronic readout array 220 incorporates radiation hardened design considerations consistent with conventional CMOS fabrication processes. These design considerations include 1) a p-well design for the active pixel circuitry and readout circuitry, and 2) radiation shielding of the non-imaging area of the sensor. The p-well design enables the use of radiation hardened p-channel transistors as the reset and select switches. The source-follower transistor is an n-channel device located in a p-well. This transistor is not required to shut off and is more tolerant to radiation damage than the reset and select transistors. The readout circuitry can be shielded with lead because it is physically located in a different area of the CMOS array than the pixel circuitry. In addition, the CMOS array is coated with selenium, which is fairly efficient at absorbing x-rays.

The radiation hardness of these sensors could be further increased by using special radiation hardened fabrication methods. These methods, however, could dramatically increase the cost of fabrication. Custom radiation hardening fabrication methods include the use of thinner oxides which require minimal tolerance in thickness and quality variations. In addition, impurities can be added to the oxide layers to allow the trapped holes to migrate out of the oxide layer.

Sensor Fabrication

The layout of electronic readout array 220 is similar to the layout of electronic readout array 190 and the layout of the circuitry associated with an individual pixel 245 is substantially similar to the layout of pixel circuit 11 described with reference to FIGS. 9 through 12. The primary difference is that readout array 220 is designed for a CMOS p-well fabrication process whereas readout array 190 is designed for an n-well fabrication process. The p-well process begins with a an n-type substrate 7. Selection transistor 260 and reset transistor 250 are p-channel transistors.

Source-follower transistor 248 is an n-channel transistor, embedded in a p-well. Readout circuitry 223 is fabricated in a similar manner as pixel circuit 245.

Readout array 220 is fabricated on a four-inch diameter crystalline silicon wafer using CMOS p-well fabrication technology in a similar manner as described for readout array 190. Readout array 220 is coated with a 1,000 micron thick layer of coated array 220 which is attached to chip carrier 221 to form a fluoroscopy image sensor 242. A voltage is applied across selenium coating amorphous selenium and a conductive electrode.

Image sensor 242 is electrically connected to two 12-bit analog-to-digital converters, each sampling at 8 megabytes/sec. This allows the entire sensor to be read in 8 msec. Another 8 msec is used to reset pixel capacitors 246 and to integrate the pixel capacitors 246 and to integrate the charge generated by x-ray irradiation. The total 16 msec image acquisition time enables a 60 Hz frame rate for image sensor 242.

Image sensor 242 is integrated into full format image sensor 240. Electrical connections from sixteen image sensors 242 are rotated to data acquisition electronics, through digital image processing electronics, and then to viewing monitor or film recorder. Image sensor 240 is integrated to one end of a conventional C-arm with 50–100 keV x-ray source attached to other end of C-arm.

ULTRAVIOLET/VISIBLE IMAGE SENSOR
Prototype Sensor

Figure 24:
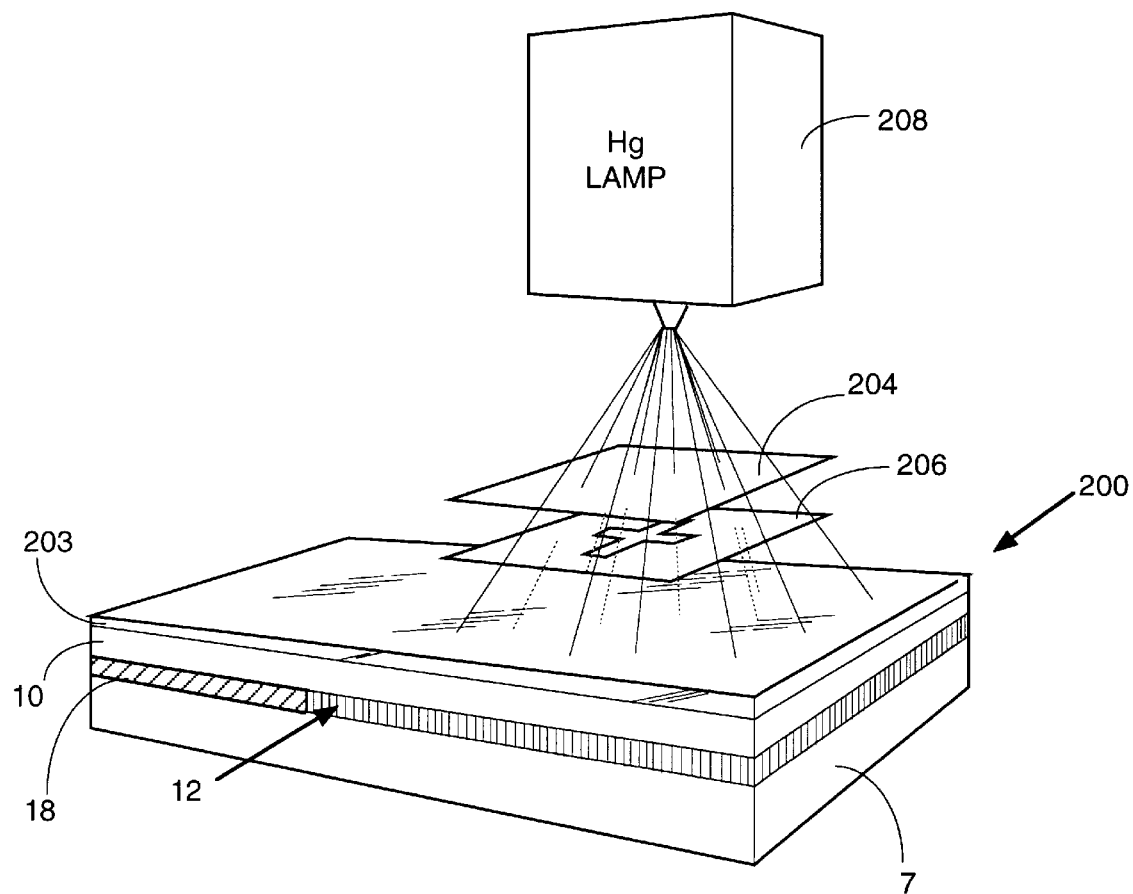
FIG. 24 is a diagram showing the principal elements of a preferred embodiment of the present invention used for ultraviolet/visible imaging.

Another embodiment of the present invention provides an image sensor for ultraviolet and visible imaging applications. A prototype embodiment of this invention, displayed in FIG. 24, is a 96×128 pixel prototype image sensor 200 which has been fabricated and tested by the inventors and their fellow workers. The 96×128 electronic readout array 12 uses the same pixel circuit as used for the 8×16 pixel prototype digital x-ray image sensor, previously described with reference to FIGS. 3 through 10. Readout array 12 is coated with a 150 micron layer of selenium 10 and then a conductive electrode 203 which is at least partially transparent to ultraviolet or visible radiation. For this electrode, the first embodiment uses a layer of sodium silicate ($Na_2SiO_3$) painted on the selenium in a water solution with liquid hand soap added to improve the wettability.

Figure 25A:
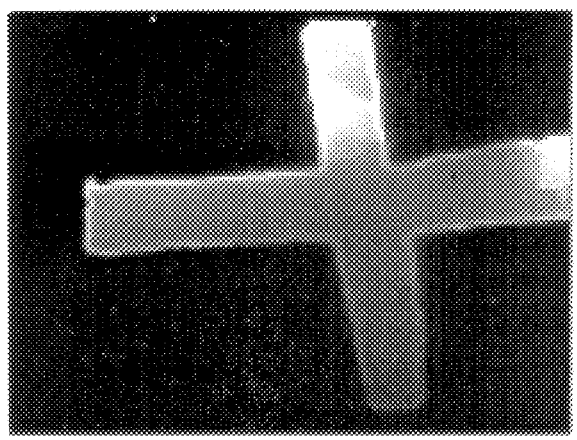
FIGS. 25A and 25B are digital printouts showing an ultraviolet image and an x-ray image, respectively, of an aperture acquired with the first preferred embodiment.
Figure 25B:
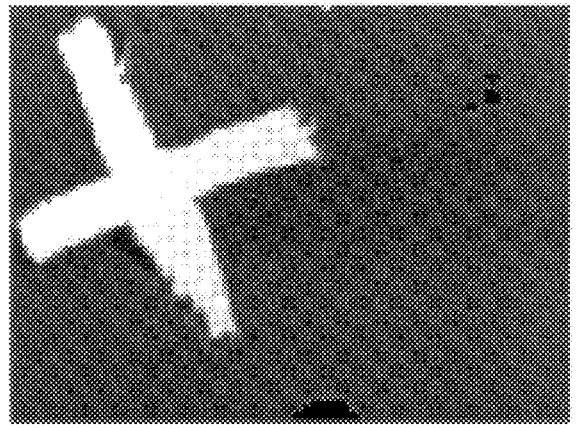

FIG. 25A displays an actual ultraviolet image acquired with the prototype ultraviolet/visible image sensor 200. For the ultraviolet image, we placed UV notch filter 204 and aperture 206 (cross-shaped) between a mercury lamp 208 and imaging sensor 200. A 600 volt (4 Volts/micron) bias voltage was applied across the selenium 10. The ultraviolet image in FIG. 25A shows the effect of a voltage drop from current flowing across the highly resistive top electrode. For comparison an x-ray (18 keV) image acquired with sensor 200 is also displayed in FIG. 25B.

Ultraviolet/Visible Image Sensor

Another embodiment of this invention for ultraviolet or visible imaging features a 512×512 pixel array with 27 micron pixels, resulting in a 1.4 cm×1.4 cm imaging area. The electronic readout array for the visible image sensor is substantially similar to readout array 220 for fluoroscopy image sensor 242 (shown in FIG. 20B) with a p-well CMOS circuit design like that shown in FIG. 21, current mode output from each sample-and-hold circuit for shorter readout times, and two current outputs.

A preferred embodiment of this image sensor uses a one-micron thick layer of hydrogenated amorphous silicon as the radiation-absorbing medium which is coated on the electronic readout array. Pure silicon in an amorphous form is not satisfactory for this purpose because there are many dangling silicon bonds in the disordered amorphous structure, and these dangling bonds result in a large number of localized states in the energy bandgap with the result that the resistivity of the material is very low. However, an improved form of amorphous silicon known as plasma-deposited hydrogenated amorphous silicon is available. It is produced by the glow-discharge dissociation of silane gas ($SiH_4$); and because it contains hydrogen atoms attached to the silicon atoms at sites that would otherwise have dangling bonds, the density of states in the energy bandgap is low and the resistivity is high enough to make this a useful semi-conductor material. By including diborane ($B_2H_6$) with the silane in the plasma chamber, the amorphous silicon is doped with boron to create a p-type material; if phosphine ($PH_3$) is included, the amorphous silicon is doped or with phosphorus to enhance the normal n-type characteristics of this material. For this preferred embodiment the amorphous silicon will be given a light doping of boron (less than 10 parts per million boron electron acceptors) in order to suppress the normal n-type behavior and increase the resistivity of the material further. This light doping controls the quantity of thermally-generated charge carriers, but it is still necessary to deal with the problem of carriers injected at the two surfaces of the amorphous silicon layer.

In the preferred embodiment, a thin (several hundredths of a micron) insulating injection-blocking layer will be required at the surface between the array and the amorphous silicon. This layer can be aluminum oxide or one of several materials such as silicon nitride or silicon oxide which can be deposited by the same plasma deposition device as the amorphous silicon. Another alternative for the blocking layer is a heavily boron-doped p-type layer of amorphous silicon (200 ppm boron, 0.3 microns thick). This layer is not insulating but instead forms a p-n junction with the bulk layer. With a positive potential of about 10 V on the top of the bulk layer this junction will be back biased and thus will not allow electrons to be injected upward into the lower surface of the bulk material, whereas positive carriers (holes) generated in the light-sensitive layer will be able to freely flow downward across the junction into the strongly p-type material. The thickness of this layer and the degree of doping should be minimized to control blurring caused by lateral conduction of charge.

For the top electrode similar considerations apply. If it is at a positive potential, it must not inject holes into the light-sensitive layer. Again the interposition of an insulating blocking layer between the top electrode and the bulk material will solve the problem, or the blocking layer could be a thin layer (less than one micron) of heavily phosphorus-doped n-type amorphous silicon. This junction would be back biased and would be unable to supply holes to the material below it but would readily accept electrons coming up from below. Then current would flow across the light-sensitive layer only when charge carrier pairs are generated in the layer by the incoming radiation. Of course, the top electrode must also be transparent to light in the desired wavelength range, and therefore will be no thicker than required to give a surface resistivity of about one megohm per square, a low enough resistivity so that lateral voltage drops from the small currents flowing in the top electrode do not disturb the acquired image. We recommend for the surface electrode indium tin oxide (a material with semiconductor properties). Other materials suitable for the transparent top electrode include very thin metal layers such as gold or platinum, or any of the conducting polymers such as polyaniline. The heavily phosphorous-doped n-type layer might also serve as the surface conductor if made sufficiently conductive.

The temperature of the substrate is one of the variable parameters for this process, and it turns out that the best ratio of photocurrent to dark current is obtained with a substrate temperature of 230 degrees C. during deposition. Fortunately, this is a temperature that the CMOS readout array will be able to tolerate for a short time without serious damage.

Figure 27:
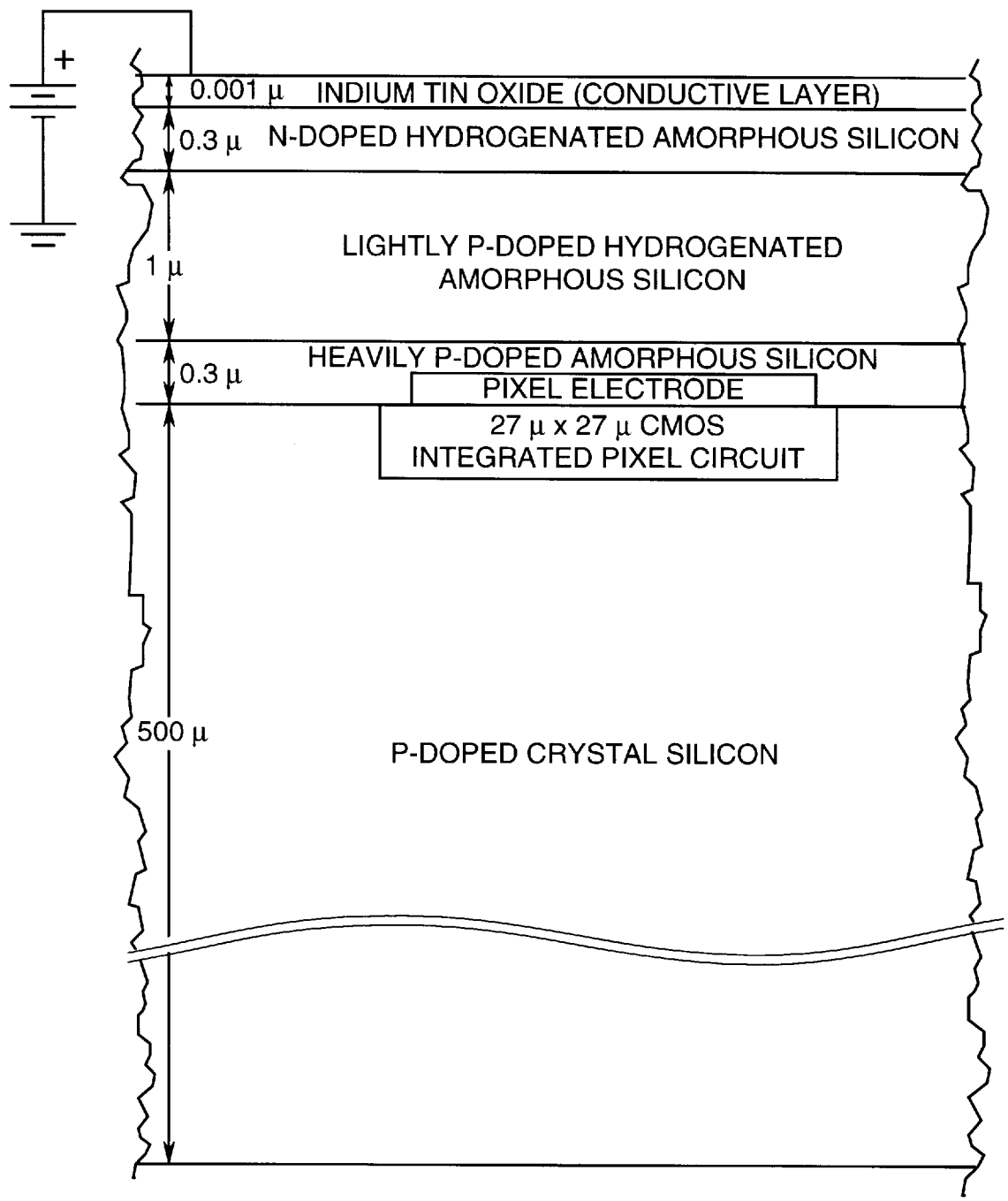
FIG. 27 is a drawing describing an ultraviolet or visible light sensor.

FIG. 27 is a drawing describing a single pixel section of a preferred embodiment of the type of sensor discussed above.

Other photoconductors are possible as well. These photoconductors can either be intrinsic materials (which have high resistivity unless illuminated by photons), or diode structures (which have small currents due to the blocking effect of the diode junction, unless illuminated). Likely candidates for visible photoconductors are cadium telluride, cadmium telluride/cadmium sulfide diode, cadmium selenide, selenium, selenium/arsenic, selenium/tellurium, and organic photoconductors such as pthalocyanine. This is not an exhaustive list, but merely examples of photoconductors which can be deposited.

Diode structures can also be run at zero applied voltage in a mode called photovoltaic. This mode has the advantage of zero current at zero light level, and could improve detector performance. We consider our usage of the term "photoconductor" to include photodiode detection as well as photovoltaic detection.

Diodes can be built in either a p-i-n or a p-n configuration. The layer contacting the electrodes should either be discontinuous or have high enough resistivity to prevent leakage between pixels. The resistivity is determined by the degree of doping.

The radiation absorbing layer can be composed of two or more separate layers composed of differing photoconductive materials. A preferred combination layer consists of a layer of cadmium telluride and a layer of cadmium sulfide. Cadmium telluride is deposited so that it is a p-type material (excessive holes). Cadmium sulfide is deposited so that it is an n-type material (excess electrons). An external voltage across the heterojunction of the two materials produces a p-n junction which acts as a photodiode. This p-n junction, is reversed biased, inhibits dark current from flowing across the junction. However, radiation induced electron-hole pairs give rise to electrical currents which flow in proportion to the incident radiation. Alternate embodiments include a p-i-n photodiode which incorporates a thin insulating layer between the p-type and n-type regions, and a Schottky photodiode which is formed between some metals and some semiconductors.

BONE DENSITOMETRY IMAGE SENSOR

Another embodiment of the present invention is a digital x-ray imaging device to image the x-ray attenuation characteristics of bone such as the forearm or the fingers, for example. Automated software analysis of these images will measure the bone mineral content. This information is then used by the physician in order to prescribe treatment for low bone mineral content.

Device Description

A preferred embodiment of the invention, displayed in FIG. 1, consists of an x-ray source and a digital x-ray image sensor. The preferred digital x-ray image sensor, displayed in FIGS. 15A and 15B, consists of a 832×1024 pixel CMOS readout array 12 with 66 micron pixels. Readout array 12 is coated with a 300 micron thick layer 10 of amorphous selenium and a conductive electrode 8. The preferred x-ray source 4 is a tungsten anode x-ray tube with x-ray output in the 30 keV to 60 keV range. X-ray source 4 and image sensor 1 are arranged in a lead lined box with a 100 cm distance between source 4 and sensor 1. A lead apodizer is placed in the path of x-rays near source 4 in order to block x-rays not directly incident on sensor 1. An opening in the lead lined box allows placement of the hand 6 or forearm in the path of x-rays. Digital data is acquired with data acquisition electronics 20 and this data is stored in computer 23 for analysis of the image data.

Image Data Acquisition and Analysis

A preferred method for bone mineral density measurement is called digital radiographic absorptiometry (DRA). This technique is described here with reference to "Radiographic Absorptiometry for Bone Mineral Measurement of the Phalanges: Precision and Accuracy Study", Seoung-Oh Yang et. al., Radiology, Vol 192, 857–859. This technique involves acquisition of a digital x-ray of at least a portion of the hand consisting of the middle phalanges (finger bones). A density standard element such as an aluminum wedge is also placed within the field of view of the image. The digital x-ray image is analyzed by a computer to compare the average x-ray attenuation in a cross-sectional slice of the middle phalange to a thickness of the aluminum wedge corresponding the same x-ray attenuation. The equivalent thickness of the aluminum wedge is used as an input to a computer algorithm which compares this value to a look-up table of previously measured ash weight of cadaver phalanges versus digital radiographic absorptiometry measurements of these cadaver phalanges. The ash weight of cadaver phalanges has been correlated to the bone mineral density and bone mineral content of a large database of patients. The comparison of the DRA measurement to a Gaussian distribution of patients in the same age group results in a single measurement consisting of a deviation from the norm of bone mineral content, expressed as a number of standard deviations (sigmas) from the norm.

The DRA technique can be further refined by providing measurements at several different sites and averaging the results. These sites can be at different locations along the middle phalange, at the two neighboring phalanges, or at the distal forearm (radius). In addition, measurements made using two slightly different x-ray energies, 30 keV and 35 keV, for example, can be averaged to make the measurement less sensitive to temporal variations in the x-ray source.

Alternate embodiments of the method involve acquisition of digital x-ray images at two x-ray energies, 30 keV and 60 keV, for example, and use of the information in the two images to remove the x-ray attenuation characteristics of the tissue surrounding the bone in order to provide a more accurate determination of the bone mineral density. The prior art for this procedure is disclosed in U.S. Pat. No. 5,150,394, Dual-Energy System for Quantitative Radiographic Imaging, by Andrew Karellas, issued Sep. 22, 1992 which is incorporated herein by reference.

Another alternate embodiment involves a characterization of the bone microstructure of the femoral neck, hip, and spine, from visual and software analysis of the acquired images.

ALTERNATE EMBODIMENTS

While the above description contains many specific details the reader should not construe these as limitations on the scope of the invention, but merely as exemplifications of preferred embodiments thereof. Those skilled in the art will envision that many other possible variations are within its scope.

For example, substrates other than single crystal silicon wafers could be used. Other such substrates include crystalline silicon on an insulator (such as silicon on sapphire or silicon or silicone oxide), aluminum gallium aresenide or indium gallium arsenide. In the future it may be possible to utilize diamond substrates. PMOS or NMOS circuits could possibly be substituted for our preferred CMOS circuits.

The prior art of thin-film transistor technology involves the coating of amorphous silicon on glass and the fabrication of circuitry on and in the amorphous silicon. The amorphous silicon has relatively low electron and hole mobility compared to crystalline silicon and this prohibits the fabrication of active circuits other than simple transistor switches in the amorphous silicon. There are a number of companies attempting to convert the coated amorphous silicon layer into pure crystalline silicon, with limited success. A specific process involves laser annealing the amorphous silicon to produce polysilicon, a silicon lattice which is locally crystalline but has a very large number of defect sites. Polysilicon has much higher electron and hole mobility and enables more elaborate circuitry to be fabricated in and on the polysilicon. It is possible in the future that a single crystal of silicon will be fabricated from an amorphous silicon coating. This single crystal will have a very low number and volume of defect sites as does the crystalline wafers utilized for CMOS fabrication. It is intended that the scope of the present invention includes the application.

We could place two of the pixel circuits 11, each depicted in FIG. 5, side by side at each pixel location. Two capacitors 78, each connected to the electrode 14 through separate switches, can store two consecutive images, without the necessity of an intermediate readout. Another embodiment involves the addition of analog-to-digital converters to each column of the electronic readout array 12.

The readout circuitry of the invention can be configured by utilizing a discriminator circuit to further reduce the accumulation of dark noise. As each x-ray photon causes a pulse of current, a comparator circuit compares the pulse height to a reference voltage. When a pulse exceeds the threshold voltage the pulse activates a trigger and a one-shot (monostable multivibrator) feeds a fixed amount of charge to the accumulation capacitor. This pulse-shaping circuit, on each pixel, results in the accumulation of a fixed amount of charge for each x-ray photon. This circuit configuration serves to reject dark current and to provide quantum limited x-ray counting. A further embodiment involves the configuration of two discriminator circuits so that high and low energy x-ray photons can be separated as a means of performing dual energy image analysis.

An alternate fabrication method for the electronic readout array 190 involves the use of a six inch diameter silicon wafer. This wafer would provide a 1536×1536 array of our 66 micron pixels 11 resulting in a 10 cm×10 cm image format. A full format 20 cm×30 cm image sensor can be fabricated by combining six of the 10 cm×10 cm image sensors in a 2×3 array.

Figure 19:
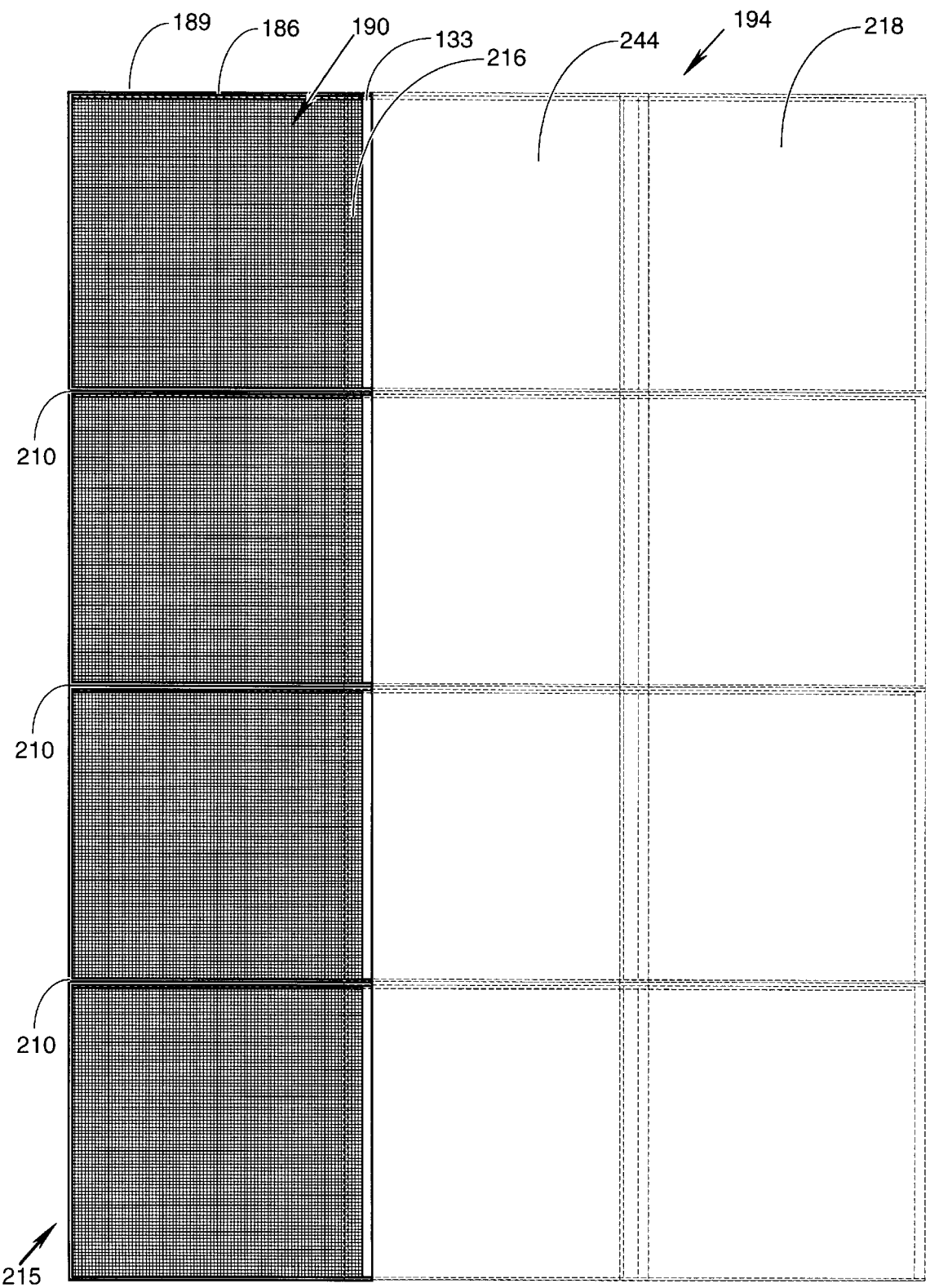
FIG. 19 is a diagram showing a method of using a strip of image sensors to sequentially image different areas of an object.

Instead of combining 12 sensors in a 3×4 sensor array to form a full-format sensor, an alternate embodiment involves the combination of four sensors 190 in a row as shown in FIG. 19. This provides a 1024×4096 pixel x-ray image sensor assembly 215 comprising an image area of approximately 6.7 cm×27 cm, with three gaps 210 approximately 1 mm×6.7 cm (approximately 15×1024 pixels) which are missing x-ray information. This sensor assembly 215 is stepped to two separate slightly overlapping positions 244 and 218 across the desired image region with an x-ray exposure at each position, and the data from the exposures are combined by the computer 23 to form a full-format image. An additional small diagonal motion in between two one-half dose exposures at each of the step positions may be employed to fill in the missing information in the gaps as well as the other missing pixels, as discussed earlier. The three strips of digital x-ray image information can be combined to form a single image by utilizing computer algorithms which provide means to register overlapping images using correlation techniques for combining the images with a blending of the overlap regions. As the sensor assembly is stepped to a new position, the tube assembly with its beam-limiting aperture is rotated about the fixed x-ray source point in order to follow the sensor assembly. The aperture limits the extent of the x-ray beam to just the sensitive area of the 1×4 sensor assembly and prevents the patient from being dosed with x-rays which do not contribute to the image.

This 1×4 array of sensors is particularly well suited to the ribbon grid concept discussed previously. In this embodiment the ribbons of tantalum or tungsten must be stretched in the direction of the principal stepping motion so that the ribbon planes remain parallel to rays fanning out from the x-ray source in each of the step positions. Since this motion direction is parallel to the short dimension of the sensor assembly, then we derive an additional benefit from the fact that the ribbon segments are short and are thus more likely to remain flat and accurately angled in accordance with the constraints at the ends of the segments. Nearly perfect flatness and angular alignments are required to minimize the number of pixels obscured by the grid. The signal values of these obscured pixels will be restored by the technique of the double exposure with a diagonal shift, as discussed above, but the overall signal-to-noise ratio in the image will suffer if too many pixels have acquired their values with only one-half of the total x-ray exposure. Furthermore, this orientation of the ribbons is the best choice for reduction of scatter. The scattered x-rays have paths with origins in the elongated region where the 1×4 aspect-ratio fan of primary x-rays intercepts the object being imaged. The scatter in directions nearly parallel to the ribbon planes is not stopped by the grid, but for this configuration that scatter is limited to a small range of angles controlled by the short dimension of the region of origin of the scattered rays. There are many more scattered rays having direction components in the direction of the long dimension of the sensor array, but most these rays will be stopped by the grid ribbons. This grid design coupled with the stepped detector assembly is more effective at removing scattered radiation than conventional grids presently being sold for mammography and is much better at preserving the intensity of the unscattered rays.

In another approach we would use a single 6.75 cm×5.5 cm selenium-coated image sensor in a mammography unit. This x-ray sensor is sequentially moved to image sixteen different areas of the breast. These slightly overlapping images are then combined in the computer using a correlation technique to form a full seamless image of the full breast.

An alternate embodiment involves the use of a very small dose of x-ray exposure to at least a small portion of a target 6, such as a breast, for example, in order to determine the optimal x-ray exposure level for the final image. The optimal x-ray exposure depends on the breast size and composition. This pre-exposure x-ray pulse can be applied to compressed breast 196 for approximately two milliseconds duration, immediately before the full x-ray exposure. The pre-exposure pulse can be applied to the full breast or to a portion of the breast by using an aperture located near the x-ray source 4. The digital information can be acquired from at least a portion of the full-format image sensor 194 and used to determine the full x-ray exposure level. One embodiment of the pre-exposure pulse involves acquiring digital information from a 100×100 array of pixels 11 located in the approximate center of the area of the final image 21 occupied by the breast 196. The average of the digital values from this 100×100 array of pixels is then used to determine the exposure level. Another alternate embodiment involves the use of three 100×100 arrays of pixels, separated so as to sample various portions of the breast 196. A weighted average of the digital information from these three arrays is then used to determine the exposure level.

An alternate embodiment of the pre-exposure x-ray pulse involves the use of at least two such pulses with different x-ray energies. The x-ray energy of the two pulses can be varied by adjusting the voltage applied to the x-ray source 4 or by changing the x-ray filter, from silver to rhodium, for example, between pulses. This information is then used to determine the optimal x-ray energy and x-ray dose for the x-ray image of the breast.

An alternate embodiment of the invention is a chest x-ray device with 125 micron square pixels on a 30 cm×45 cm image area. This image format can be achieved by combining twelve 10 cm×10 cm image sensors in a 3×4 sensor array, in a manner similar to that depicted in FIGS. 17A and 17B, or by combining four 10 cm×10 cm sensors in a row, and sequentially stepping the assembly to three different positions to acquire the full format image.

Chest x-ray images typically require x-rays with photon energies centered at 60 to 70 keV. The selenium layer 10 will be 1200 microns thick to absorb most of these incident x-rays.

Alternatively, the radiation absorbing layer 10 would be comprised of lead oxide, which has an absorption constant which is four times higher than selenium. A 300 micron layer of lead oxide will absorb most of the x-rays between 60 and 70 keV.

The invention can be used to image electrical circuit boards. Preferred radiation for this application is 60–70 keV x-ray photons, and 1,000 microns of selenium are required to absorb most of the x-ray photons. The preferred embodiment has 25 micron square pixels over a 3 cm square image area.

An alternate embodiment for the invention is a sensor for x-ray computed tomography (x-ray CT) imaging devices. This embodiment utilizes a fan-beam x-ray source which is detected by a partial arc of x-ray detectors located opposite the x-ray source. The preferred sensor includes 480 pixel elements, each element two millimeters square, arranged on a 46 cm radius circular arc. Each sensor element has a 1200 micron thick layer of selenium to absorb most of the 70 keV x-ray photons. The x-ray source and sensor rotate around a target and x-ray information is acquired from all the pixel elements for discrete angular locations of the rotating source and sensor. The x-ray information is used in mathematical reconstruction algorithms to form a tomographic image of the target using well known techniques.

For special applications we would also apply the principles of this invention with other radiation sources such as alpha or beta radiation.

The fabrication of large format x-ray image sensors with CMOS readout arrays typically requires combining multiple smaller arrays, either by butting or shingling. An alternate embodiment for combining arrays involves fabrication of a four-side buttable array with the readout circuitry integrated with the pixel array. This design is possible with the larger pixel size fluoroscopy image sensor where the pixel circuitry in each pixel occupies a small fraction (15%) of the 200 micron pixel area. The sample-and-hold circuits, shift registers, and analog-multiplexers are integrated within the remaining areas not occupied by the pixel circuits. Wire bond connections are made to select pixel locations at the periphery of the array. These pixel locations are treated as dead pixels. Wire bond connections are made on the top of the array or could be brought down the side of the array to connect on the bottom of the array. The preferred embodiment features a 70×70 pixel array with 200 micron pixels resulting in a 1.4×1.4 cm cm image area. This design is the maximum size suitable for a 1.2 micron CMOS p-well fabrication process. These arrays are butted together in strips of ten and attached to a substrate such as FR4 circuit board material, for example. Adjacent arrays are wire bonded together in a daisy-chain fashion utilizing the wire bond pads at the periphery of the arrays. Preferably, ten strips are arranged in a 14 cm×14 cm image array by butting these strips together. The resulting 14 cm×14 cm image array is coated with selenium and a conductive electrode to form a fluoroscopy image sensor. An alternate embodiment involves placing the uncoated 14 cm×14 cm image array in a vessel of high pressure Xenon gas, which is used as the photoconductive material. Alternate embodiments include coating the strips with selenium and conductive electrode and then assembling the strips or coating individual arrays with selenium and conductive electrodes and then assembling the strips.

Photoconductive materials other than selenium and lead oxide can be used as the absorbing layer for x-ray radiation. Preferably the layer will be thick enough to absorb most of the radiation. Other materials include amorphous silicon, lead sulfide, zinc oxide, zinc sulfide, cadmium telluride, cadmium selenide, zinc selenide, zinc telluride, cadmium sulfide, lead iodide antimony trysulfide, and diamond film. In addition, various gases can be used a photoconductors, including xenon and krypton.

Selenium has a photoconductive response in the spectral range from x-rays to visible light, becoming less responsive in the spectral region beyond 500 nm. The addition of 70% tellerium to selenium raises the photoconductive response in the visible region and extends the response to 800 nm.

Accordingly, the reader is requested to determine the scope of the invention by the appended claims and their legal requirements, and not by the examples which have been given.

We claim:

1. An imaging device for producing images from electron-hole producing radiation comprising:
   A. at least one solid state radiation detection unit comprising:
      1) a substrate comprised of a doped crystalline semiconductor material,
      2) a plurality of metal oxide semiconductor pixel circuits incorporated into and on said substrate to form an array, defining an array of pixel circuits, each of said semiconductor pixel circuits defining a pixel and comprising:
         a) a charge collecting pixel electrode,
         b) a pixel capacitor defined at least in part by said charge collecting electrode for storing charges collected by said charge collecting electrode,
         c) a charge measuring circuit comprising a single transistor amplifier for permitting a measurement of charge stored on said pixel capacitor,
      3) a radiation absorbing layer comprised of an electrically insulating photoconductive material covering said array of pixel circuits, said material being photoconductive on exposure to said electron-hole producing radiation,
      4) a surface electrode layer comprised of electrically conducting material deposited on said radiation absorbing layer, said electrode layer being at least partially transparent to said radiation, and connectable to a voltage source for establishing an electrical field across said radiation absorbing layer and between said surface electrode layer and said charge collecting electrodes;
   B. a pixel charge measurement circuit for measuring charges stored on each of said pixel capacitors via said measuring circuits, and outputting pixel data indicative of such charges, wherein said pixel data contains information defining an image.

2. An imaging device as in claim 1 wherein said substrate is comprised of doped single crystal silicon.

3. An imaging device as in claim 2 wherein said substrate is a wafer.

4. An imaging device as in claim 2 wherein each of said pixel capacitors is comprised of an insulating oxide layer sandwiched between two heavily doped polycrystalline silicon layers.

5. An imaging device as in claim 4 wherein said oxide layer is $SiO_2$ glass.

6. An imaging device as in claim 2 wherein said single crystal silicon substrate is doped to create n-type silicon.

7. An imaging device as in claim 2 wherein said single crystal silicon substrate is doped to create p-type silicon.

8. An imaging device as in claim 1 wherein said substrate is comprised of silicon on an electrical insulator.

9. An imaging device as in claim 8 wherein said insulator is comprised of silicon oxide or sapphire.

10. An imaging device as in claim 1 wherein said substrate is comprised of aluminum gallium arsenide.

11. An imaging device as in claim 1 wherein said substrate is comprised of indium gallium arsenide.

12. An imaging device as in claim 1 wherein said metal oxide semiconductor pixel circuits are complimentary metal oxide semiconductor pixel circuits.

13. An imaging device as in claim 1 wherein said metal oxide semiconductor pixel circuits are n-channel metal oxide semiconductor pixel circuits.

14. An imaging device as in claim 1 wherein said metal oxide semiconductor pixel circuits are p-channel metal oxide semiconductor pixel circuits.

15. An imaging device as in claim 1 wherein said electron-hole producing radiation comprises x-ray radiation.

16. An imaging device as in claim 1 wherein said electron-hole producing radiation comprises ultraviolet radiation.

17. An imaging device as in claim 1 wherein said electron-hole producing radiation comprises visible light.

18. An imaging device as in claim 1 wherein said electron-hole producing radiation comprises particle radiation.

19. An imaging device as in claim 1 and further comprising data acquisition system for acquiring and storing said pixel data and a monitor for display of said image.

20. An imaging device as in claim 1 and further comprising data acquisition system for acquiring and storing said pixel data and a printer for printing said image.

21. An imaging device as in claim 1 wherein each charge collecting pixel electrode is comprised of aluminum.

22. An imaging device as in claim 1 wherein each charge measuring circuit further comprises a second field effect transistor, coupled to the single transistor amplifier, and arranged in an electrical circuit so as to permit non-destructive measurement of said charge.

23. An imaging device as in claim 22 wherein said single transistor amplifier comprises a source follower transistor and said second field effect transistor comprises a selection transistor.

24. An imaging device as in claim 23 wherein each pixel capacitor defines two parallel plates and said source follower transistor defines a gate and one of said plates is electrically connected to said gate.

25. An imaging device as in claim 24 wherein said each of said metal oxide semiconductor pixel circuits also comprises a reset transistor means for resetting each of said pixel circuits.

26. An imaging device as in claim 25 wherein each of said reset transistor means comprises an electrical circuit for shorting the associated pixel capacitor to ground.

27. An imaging device as in claim 26 wherein each reset transistor means comprises a back biased reset transistor.

28. An imaging device as in claim 1 wherein said photoconductive material comprises amorphous selenium.

29. An imaging device as in claim 28 wherein said selenium is deposited as a film.

30. An imaging device as in claim 29 wherein said film is vapor deposited.

31. An imaging device as in claim 30 wherein said selenium is alloyed with arsenic.

32. An imaging device as in claim 1 wherein said surface electrode layer is silver, indium tin oxide, gold, platinum, or a conducting polymer.

33. An imaging device as in claim 1 further including a voltage source, wherein said voltage source is arranged to produce an electric field in said radiation absorbing layer of between 2 and 20 volts per micron.

34. An imaging device as in claim 1 wherein said photoconductive material is comprised of at least two layers of photoconductive material.

35. An imaging device as in claim 34 wherein said at least two layers define a photodiode.

36. An imaging device as in claim 35 wherein said photodiode comprises a p-n junction.

37. An imaging device as in claim 35 wherein said photodiode comprises a p-i-n junction.

38. An imaging device as in claim 35 wherein said photodiode comprises a Schottky junction.

39. An imaging device as in claim 1 wherein said charge collecting pixel electrodes are separated from said surface electrode layer by a thickness of at least 10 microns of said photoconductive material.

40. An imaging device as in claim 1 wherein said array is arranged to form rows and columns and said pixel charge measurement circuit comprises a sample and hold circuit at each column with a shift register for selection of rows and a separate shift register for selection of columns.

41. An imaging device as in claim 40 further including a data acquisition system for acquiring and storing said pixel data, wherein said data acquisition system comprises an analog to digital converter.

42. An imaging device as in claim 1 further including a voltage source, wherein said voltage source is electrically arranged so as to provide positive voltage at said surface electrode layer with respect to said charge collecting electrodes.

43. An imaging device as in claim 1 further including a voltage source, wherein said voltage source is electrically arranged so as to provide a negative voltage at said surface electrode layer with respect to said charge collecting electrodes.

44. An imaging device as in claim 1 wherein said at least one detection unit is a plurality of detection units.

45. An imaging device as in claim 44 wherein said plurality of detection units comprises at least one row of at least four detection units.

46. An imaging device as in claim 45 wherein said at least one row is at least three rows arranged parallel to each other.

47. An imaging device as in claim 1 and further comprising a computer for computing images from said pixel data.

48. An imaging device as in claim 1 wherein said imaging device is installed as an element of a bone densitometry system.

49. An imaging device as in claim 48 and further comprising a computer programmed with an algorithm for determining bone density based on said pixel data.

50. An imaging device as in claim 49 and further comprising a density standard element positioned in the path of said electron-hole producing radiation.

51. An imaging device as in claim 50 wherein said pixel data, used for determination of bone density, comprises at least two sets of data, each set corresponding to radiation at a selected x-ray energy.

52. An imaging device for producing images of a target irradiated with electron-hole producing radiation comprising:

A. radiation source producing a beam of said electron-hole producing radiation directed at said target, said beam defining a beam path, B. at least one solid state radiation detection unit positioned in said beam path downstream of said target, said unit comprising:
1) a substrate comprised of doped single crystal silicon,
2) a plurality of complementary metal oxide semiconductor pixel circuits incorporated into and on said single crystal silicon to form an array, defining an array of pixel circuits, each of said semiconductor pixel circuits defining a pixel and comprising
   a) a charge collecting pixel electrode,
   b) a pixel capacitor defined at least in part by said charge collecting electrode for storing charges collected by said charge collecting electrode,
   c) a charge measuring circuit comprising a single transistor amplifier for permitting a measurement of charge stored on said pixel capacitor,
3) a radiation absorbing layer comprised of an electrically insulating photoconductive material covering said array of pixel circuits, said material being photoconductive on exposure to said electron-hole producing radiation,
4) a surface electrode layer comprised of electrically conducting material deposited on said radiation absorbing layer, said electrode layer being at least partially transparent to said radiation, and
5) voltage source establishing an electrical field across said radiation absorbing layer and between said surface electrode layer and said charge collecting electrodes;

C. a pixel charge measurement circuit for making measurements of charges stored on each of said pixel capacitors via said measuring circuits, and outputting pixel data indicative of such charges, D. a data acquisition system for acquiring and storing said pixel data, E. a computer for computing images of said target from said pixel data.

53. An imaging device as in claim 52 wherein said electron-hole producing radiation comprises x-ray radiation.

54. An imaging device as in claim 53 wherein said at least one detection unit is a plurality of detection units arranged in at least one row of at least four detection units.

55. An imaging device as in claim 54 and further comprising a positioning means for moving said at least one row of detection units relative to said target.

56. An imaging device as in claim 55 and further comprising an anti-scatter grid placed between said target and said detection units.

57. An imaging device as in claim 56 wherein said anti-scatter grid is fixed with respect to said detection units.

58. An imaging device as in claim 55 wherein said computer comprises software to generate a composite image of at least a portion of said target from a plurality of images of portions of said target.

59. An imaging device as in claim 55 wherein said source, said positioning means and said at least one detection unit are configured so as to image at least a portion of a human body.

60. An imaging device as in claim 59 wherein said imaging device is utilized to image the female breast.

61. An imaging device as in claim 55 wherein said computer is programmed with an algorithm for blending pixel values to produce seamless images.

62. An imaging device as in claim 53 wherein said at least one detection unit is a plurality of detection units arranged in a plurality of rows and a plurality of columns, and further comprising a positioning means for moving said detection units relative to said target in order to acquire a plurality of overlapping images of portions of said target.

63. An imaging device as in claim 62 wherein said positioning means moves the detections units diagonally.

64. An imaging device as in claim 62 wherein said computer comprises software to generate a composite image of at least a portion of said target from a plurality of overlapping images of portions of said target.

65. An imaging device as in claim 62 wherein said computer comprises software to cause the positioning means to acquire a first image of a portion of said target, move said detection units relative to said target, acquire at least a second, overlapping image of a portion of said target, and generate a composite image of at least a portion of said target from the overlapping acquired images.

66. An imaging device as in claim 65 wherein each said image is acquired at a low x-ray dosage such that the combined x-ray dosage of all images is within a medically acceptable limit.

67. An imaging device as in claim 52 and further comprising an x-ray dose limiting means for limiting x-ray dose to said target.

68. An imaging device as in claim 67 wherein said dose limiting means comprises a means for collecting pre-exposure x-ray data.

69. An imaging device as in claim 68 and further comprising spectrum selection means for selecting an x-ray spectrum based on said pre-exposure x-ray data.

70. An imaging device as in claim 52 wherein said source, and said at least one detection unit are configured to image an electronic circuit board.

71. An imaging device as in claim 52 wherein said source, and said at least one detection unit are configured to provide an x-ray computed tomography device.

72. An imaging device as in claim 52 wherein said photoconductive material comprises amorphous selenium doped with tellurium.

73. An imaging device as in claim 72 wherein said electron-hole producing radiation comprises visible radiation.

74. An imaging device as in claim 72 wherein said electromagnetic radiation comprises infrared radiation.

75. An imaging device as in claim 52 wherein said substrate is a wafer.

76. An imaging device as in claim 52 wherein each of said pixel circuits comprises a reset switch and a reset line.

77. An imaging device as in claim 76 wherein each of said pixel circuits comprises an isolation means to isolate said circuits from said reset line.

78. An imaging device as in claim 52 wherein each of said plurality of pixel circuits comprises a second pixel capacitor connected to said charge collecting pixel electrode.

79. An imaging device as in claim 52 wherein said device is configured to make chest x-ray images.

80. An imaging device as in claim 52 wherein said device is configured to image integrated circuit boards.

81. An imaging device as in claim 52 wherein said devices is configured to make tomographic images.

82. An imaging device for producing images from electron-hole producing radiation comprising:
   A. at least one solid state radiation detection unit comprising:
      1) a substrate comprised of a doped crystalline semiconductor material,
      2) a plurality of metal oxide semiconductor pixel circuits incorporated into and on said substrate to form an array, defining an array of pixel circuits, each of said semiconductor pixel circuits defining a pixel and comprising:
         a) a charge collecting pixel electrode,
         b) a pixel capacitor defined at least in part by said charge collecting electrode for storing charges collected by said charge collecting electrode,
         c) a charge measuring circuit comprising a single transistor amplifier for permitting a measurement of charge stored on said pixel capacitor,
      3) a radiation absorbing layer comprised of at least two sublayers of an electrically insulating photoconductive material covering said array of pixel circuits, said at least two sublayers being photoconductive on exposure to said electron-hole producing radiation, said at least two sublayers forming a semiconductor junction,
      4) a surface electrode layer comprised of electrically conducting material deposited on said radiation absorbing layer, said electrode layer being at least partially transparent to said radiation,
   B. a pixel charge measurement circuit for measuring charges stored on each of said pixel capacitors via said measuring circuits, and outputting pixel data indicative of such charges, wherein said pixel data contains information defining an image.

83. An imaging device as in claim 82 wherein said semiconductor junction is a p-n junction.

84. An imaging device as in claim 82 wherein said semiconductor junction is a p-i-n junction.

* * * * *